US010662234B2

(12) United States Patent
Sandrasagra et al.

(10) Patent No.: US 10,662,234 B2
(45) Date of Patent: May 26, 2020

(54) METHODS FOR REPAIRING TISSUE DAMAGE USING PROTEASE-RESISTANT MUTANTS OF STROMAL CELL DERIVED FACTOR-1

(75) Inventors: Anthony Sandrasagra, Arlington, MA (US); Weitao Wu, Malden, MA (US)

(73) Assignee: Mesoblast International Sàrl, Meyrin (CH)

( * ) Notice: Subject to any disclaimer, the term of this patent is extended or adjusted under 35 U.S.C. 154(b) by 0 days.

(21) Appl. No.: 14/124,187

(22) PCT Filed: Jun. 6, 2012

(86) PCT No.: PCT/US2012/041054
§ 371 (c)(1),
(2), (4) Date: Jan. 6, 2014

(87) PCT Pub. No.: WO2012/170495
PCT Pub. Date: Dec. 13, 2012

(65) Prior Publication Data
US 2014/0199304 A1 Jul. 17, 2014

Related U.S. Application Data

(60) Provisional application No. 61/494,079, filed on Jun. 7, 2011.

(51) Int. Cl.
*C07K 14/52* (2006.01)
*A61K 38/04* (2006.01)
*A61K 38/08* (2019.01)
*A61K 38/16* (2006.01)
*A61K 38/19* (2006.01)

(52) U.S. Cl.
CPC ............ *C07K 14/522* (2013.01); *A61K 38/19* (2013.01); *C07K 2319/30* (2013.01)

(58) Field of Classification Search
None
See application file for complete search history.

(56) References Cited

U.S. PATENT DOCUMENTS

| | | | | |
|---|---|---|---|---|
| 5,171,680 | A | 12/1992 | Mullenbach et al. | |
| 5,563,048 | A | 10/1996 | Honjo et al. | |
| 5,670,483 | A | 9/1997 | Zhang et al. | |
| 5,756,084 | A | 5/1998 | Honjo et al. | |
| 6,100,387 | A | 8/2000 | Herrmann et al. | |
| 6,214,540 | B1 | 4/2001 | DeVico et al. | |
| 6,221,856 | B1 | 4/2001 | Traynor-Kaplan et al. | |
| 6,440,934 | B1 * | 8/2002 | Whitehouse | 514/9.1 |
| 6,548,630 | B1 | 4/2003 | Zhang et al. | |
| 6,852,508 | B1 | 2/2005 | Herrmann et al. | |
| 6,875,738 | B1 | 4/2005 | Clark-Lewis et al. | |
| 6,946,445 | B1 | 9/2005 | Clark-Lewis et al. | |
| 7,354,899 | B2 | 4/2008 | Clark-Lewis et al. | |
| 7,368,425 | B2 | 5/2008 | Merzouk et al. | |
| 7,378,098 | B2 | 5/2008 | Tudan et al. | |
| 7,435,718 | B2 | 10/2008 | Tudan et al. | |
| 7,485,141 | B2 | 2/2009 | Majercak et al. | |
| 7,527,946 | B2 * | 5/2009 | Whitty et al. | 435/69.51 |
| 7,547,674 | B2 | 6/2009 | Anversa et al. | |
| 7,662,392 | B2 | 2/2010 | Itescu | |
| 7,696,309 | B2 | 4/2010 | Lee et al. | |
| 7,999,067 | B2 | 8/2011 | Lee et al. | |
| 8,414,924 | B2 | 4/2013 | Oh et al. | |
| 8,496,931 | B2 | 7/2013 | Pogue et al. | |
| 9,175,267 | B2 | 11/2015 | Gronthos et al. | |
| 9,308,277 | B2 | 4/2016 | Segers et al. | |
| 9,631,005 | B2 | 4/2017 | Lee et al. | |
| 2002/0094327 | A1 | 7/2002 | Petersen | |
| 2002/0107195 | A1 | 8/2002 | Gupta | |
| 2002/0107196 | A1 | 8/2002 | Gupta | |
| 2002/0111290 | A1 | 8/2002 | Homey et al. | |
| 2002/0156023 | A1 | 10/2002 | Walling et al. | |
| 2002/0165123 | A1 | 11/2002 | Tudan et al. | |
| 2003/0176780 | A1 | 9/2003 | Arnold et al. | |
| 2003/0199464 | A1 | 10/2003 | Itescu | |
| 2003/0215792 | A1 | 11/2003 | Muller et al. | |
| 2004/0037811 | A1 | 2/2004 | Penn et al. | |
| 2004/0110710 | A1 | 6/2004 | Wang et al. | |
| 2004/0247564 | A1 | 12/2004 | Itescu | |
| 2005/0020528 | A1 | 1/2005 | Herrmann et al. | |
| 2005/0059584 | A1 | 3/2005 | Merzouk et al. | |
| 2005/0065064 | A1 | 3/2005 | Lolis et al. | |
| 2005/0142101 | A1 | 6/2005 | Forssmann et al. | |
| 2005/0271639 | A1 | 12/2005 | Penn et al. | |
| 2006/0088510 | A1 | 4/2006 | Lee et al. | |
| 2006/0110374 | A1 | 5/2006 | Czeiger et al. | |
| 2006/0148703 | A1 | 7/2006 | Lee et al. | |
| 2007/0060512 | A1 | 3/2007 | Sadeghi et al. | |
| 2007/0172811 | A1 | 7/2007 | Srivastava et al. | |
| 2007/0203062 | A1 | 8/2007 | Ellis-Behnke et al. | |
| 2007/0224171 | A1 | 9/2007 | Penn et al. | |
| 2007/0258943 | A1 | 11/2007 | Penn et al. | |

(Continued)

FOREIGN PATENT DOCUMENTS

| | | | |
|---|---|---|---|
| CN | 101553243 | A | 10/2009 |
| JP | H07-501217 | A | 2/1995 |

(Continued)

OTHER PUBLICATIONS

U.S. Appl. No. 13/029,891, filed Feb. 17, 2011.*

(Continued)

*Primary Examiner* — Elizabeth C. Kemmerer
(74) *Attorney, Agent, or Firm* — Clark & Elbing LLP

(57) ABSTRACT

The present invention features methods for treating or ameliorating tissue damage using intravenous administration of compositions that include stromal cell derived factor-1 (SDF-1) peptides or mutant SDF-1 peptides that have been mutated to make them resistant to protease digestion, but which retain chemoattractant activity. Systemic delivery, and specifically intravenous ("IV") delivery, of SDF-1 and protease resistant SDF-1 mutants is very effective for the treatment of tissue damage.

20 Claims, 1 Drawing Sheet

Specification includes a Sequence Listing.

(56) References Cited

U.S. PATENT DOCUMENTS

| | | | |
|---|---|---|---|
| 2008/0095758 A1 | 4/2008 | Lee et al. | |
| 2008/0194478 A1 | 8/2008 | Colin et al. | |
| 2008/0253996 A1 | 10/2008 | Boschert et al. | |
| 2009/0029912 A1 | 1/2009 | Gronthos et al. | |
| 2009/0285785 A1 | 11/2009 | Jimi et al. | |
| 2010/0166717 A1 | 7/2010 | Penn | |
| 2010/0267612 A1* | 10/2010 | Tabata | 514/1.1 |
| 2010/0304477 A1 | 12/2010 | Buscher et al. | |
| 2011/0014691 A1 | 1/2011 | Menasche et al. | |
| 2011/0159099 A1 | 6/2011 | Yasuda et al. | |
| 2011/0269685 A1 | 11/2011 | Lee et al. | |
| 2012/0157381 A1* | 6/2012 | Spees | 514/8.1 |
| 2012/0165392 A1 | 6/2012 | Olson et al. | |
| 2016/0303197 A1 | 10/2016 | Sandrasagra et al. | |
| 2016/0375100 A1 | 12/2016 | Segers et al. | |
| 2017/0101451 A1 | 4/2017 | Lee et al. | |

FOREIGN PATENT DOCUMENTS

| | | | |
|---|---|---|---|
| JP | 2007-537752 | A | 12/2007 |
| JP | 2010-507391 | A | 3/2010 |
| WO | WO-02/38172 | A2 | 5/2002 |
| WO | WO-2004/017978 | A1 | 3/2004 |
| WO | WO-2004/094465 | A2 | 11/2004 |
| WO | WO-2005/116192 | A2 | 12/2005 |
| WO | WO-2006/032075 | A1 | 3/2006 |
| WO | WO-2006/047315 | A2 | 5/2006 |
| WO | WO-2006/073889 | A2 | 7/2006 |
| WO | WO-2006/074464 | A2 | 7/2006 |
| WO | WO-2006/124013 | A2 | 11/2006 |
| WO | WO-2007/079460 | A2 | 7/2007 |
| WO | WO-2008/051505 | A2 | 5/2008 |
| WO | WO 2012/026041 | A1 * | 3/2011 |
| WO | WO-2011/106234 | A1 | 9/2011 |
| WO | WO-2012/027170 | A1 | 3/2012 |
| WO | WO-2012/170495 | A1 | 12/2012 |
| WO | WO-2015/089396 | A1 | 6/2015 |

OTHER PUBLICATIONS

PMID 21403096, in PubMed Database, National Center for Biotechnology Information, Bethesda, Maryland, USA [online], [retrieved on Aug. 7, 2015]. Retrieved from the Internet: <URL:http://www.ncbi.nlm.nih.gov/pubmed/?term=21403096>.*

European Search Report for European Patent Application No. 12796309.8, dated Jan. 28, 2015 (7 pages).

Office Action for Chinese Application No. 201280037907.4, dated Nov. 3, 2014 (English Translation Included) (19 pages).

Petit et al., "The SDF-1-CXCR4 signaling pathway: a molecular hub modulating neo-angiogenesis," Trends in Immunol. 28(7):299-307 (2007).

Askari et al., "Effect of stromal-cell-derived factor 1 on stem-cell homing and tissue regeneration in ischaemic cardiomyopathy," Lancet. 362(9385):697-703 (2003).

Badillo et al., "Lentiviral gene transfer of SDF-1alpha to wounds improves diabetic wound healing," J Surg Res. 143(1):35-42 (2007).

Bowie et al., "Deciphering the message in protein sequences: tolerance to amino acid subsitutions," Science. 247(4948):1306-10 (1990).

Carr et al., "Efficacy of systemic administration of SDF-1 in a model of vascular insufficiency: support for an endothelium-dependent mechanism," Cardiovasc Res. 69(4):925-35 (2006).

Chang et al., "Regenerative therapy for stroke," Cell Transplant. 16(2):171-81 (2007).

Chen et al., "Site-specific labeling of cell surface proteins with biophysical probes using biotin ligase," Nat Methods. 2(2):99-104 (2005).

Cosset et al., "High-titer packaging cells producing recombinant retroviruses resistant to human serum," J Virol. 69(12):7430-6 (1995).

Crump et al., "Solution structure and basis for functional activity of stromal cell-derived factor-1; dissociation of CXCR4 activation from binding and inhibition of HIV-1," EMBO J. 16(23):6996-7007 (1997).

Cui et al., "Nitric oxide donor upregulation of stromal cell-derived factor-1/chemokine (CXC motif) receptor 4 enhances bone marrow stromal cell migration into ischemic brain after stroke," Stem Cells. 25(11):2777-85 (2007).

Davis et al., "Local myocardial insulin-like growth factor 1 (IGF-1) delivery with biotinylated peptide nanofibers improves cell therapy for myocardial infarction," Proc Natl Acad Sci U S A. 103(21):8155-60 (2006).

De La Luz Sierra et al., "Differential processing of stromal-derived factor-1alpha and stromal-derived factor-1beta explains functional diversity," Blood. 103(7):2452-9 (2004).

Di Rocco et al., "Enhanced healing of diabetic wounds by topical administration of adipose tissue-derived stromal cells overexpressing stromal-derived factor-1: biodistribution and engraftment analysis by bioluminescent imaging," Stem Cells Int. 2011(304562): 1-11 (2010).

Elmadbouh et al., "Ex vivo delivered stromal cell-derived factor-1alpha promotes stem cell homing and induces angiomyogenesis in the infarcted myocardium," available in PMC Sep. 28, 2009, published in final edited form as: J Mol Cell Cardiol. 42(4):792-803 (2007).

Gallagher et al., "Diabetic impairments in NO-mediated endothelial progenitor cell mobilization and homing are reversed by hyperoxia and SDF-1 alpha," J Clin Invest. 117(5):1249-59 (2007).

Heveker et al., "Pharmacological properties of peptides derived from stromal cell-derived factor 1: study on human polymorphonuclear cells," Mol Pharmacol. 59(6):1418-1425 (2001).

Hiasa et al., "Gene transfer of stromal cell-derived factor-1alpha enhances ischemic vasculogenesis and angiogenesis via vascular endothelial growth factor/endothelial nitric oxide synthase-related pathway: next-generation chemokine therapy for therapeutic neovascularization," Circulation. 109(20):2454-61 (2004).

Hsieh et al., "Controlled delivery of PDGF-BB for myocardial protection using injectable self-assembling peptide nanofibers," J Clin Invest. 116(1):237-48 (2005).

Kanki et al., "Stromal cell-derived factor-1 retention and cardioprotection for ischemic myocardium," Circ Heart Fail. 4(4):509-18 (2011).

Koch et al., "Effect of catheter-based transendocardial delivery of stromal cell-derived factor lalpha on left ventricular function and perfusion in a porcine model of myocardial infarction," Basic Res Cardiol. 101(1):69-77 (2006).

Kryczek et al., "Stroma-derived factor (SDF-1/CXCL12) and human tumor pathogenesis," Am J Physio Cell Physiol. 292(3):C987-95 (2007).

Lambeir et al., "Kinetic investigation of chemokine truncation by CD26/dipeptidyl peptidase IV reveals a striking selectivity within the chemokine family," J Biol Chem. 276(32):29839-45 (2001).

Lapidot et al., "How do stem cells find their way home?" Blood. 106(6):1901-10 (2005).

Loetscher et al., "N-terminal peptides of stromal cell-derived factor-1 with CXC chemokine receptor 4 agonist and antagonist activities," J Biol Chem. 273(35):22279-83 (1998).

McQuibban et al., "Matrix metalloproteinase activity inactivates the CXC chemokine stromal cell-derived factor-1," J Biol Chem. 276(47):43503-8 (2001).

Medical Technology 3-DM Inc. Products, Introduction, Puramatrix, http//www.puramatrix.com/pr01.html, Retrieved on Sep. 3, 2009 (1 page).

Mirshahi et al., "SDF-1 activity on microvascular endothelial cells: consequences on angiogenesis in in vitro and in vivo models," Thromb Res. 99(6):587-94 (2000).

Nagasawa et al., "Defects of B-cell lymphopoiesis and bone-marrow myelopoiesis in mice lacking the CXC chemokine PBSF/SDF-1," Nature. 382(6592):635-8 (1996).

Netzel-Arnett et al., "Comparative sequence specificities of human 72- and 92-kDa gelatinases (type IV collagenases) and PUMP (matrilysin)," Biochemistry. 32(25):6427-32 (1993).

(56) References Cited

OTHER PUBLICATIONS

Ngo et al., *The Protein Folding Problem and Tertiary Structure Prediction*, Merz and Le Grand, Springer Verlag, 433 and 492-495 (1994).
Ohab et al., "A neurovascular niche for neurogenesis after stroke," J Neurosci. 26(50):13007-16 (2006).
Ohnishi et al., "Crystal structure of recombinant native SDF-1alpha with additional mutagenesis studies: an attempt at a more comprehensive interpretation of accumulated structure-activity relationship data," J Interferon Cytokine Res. 20(8):691-700 (2000).
Penn et al., "Role of stem cell homing in myocardial regeneration," Int J Cardiol. 95(Suppl 1):S23-5 (2004).
Peterson et al., "Evolution of matrix metalloprotease and tissue inhibitor expression during heart failure progression in the infarcted rat," Cardiovasc Res. 46(2):307-15 (2000).
Pillarisetti et al., "Cloning and relative expression analysis of rat stromal cell derived factor-1 (SDF-1)1: SDF-1 alpha mRNA is selectively induced in rat model of myocardial infarction," Inflammation. 25(5):293-300 (2001).
Rosenblum et al., "Prolyl peptidases: a serine protease subfamily with high potential for drug discovery," Curr Opin Chem Biol. 7(4):496-504 (2003).
Sasaki et al., "Stromal cell-derived factor-1alpha improves infarcted heart function through angiogenesis in mice," Pediatr Int. 49(6):966-71 (2007).
Saxena et al., "Stromal cell-derived factor-1alpha is cardioprotective after myocardial infarction," Circulation. 117(17):2224-31 (2008).
Schubert, "Measurement of oral tissue damage and musositis pain," http://painresearch.utah.edu/cancerpain/ch15.html, retrieved Nov. 4, 2011, (1-16).
Segers et al., "Local delivery of protease-resistant stromal cell derived factor-1 for stem cell recruitment after myocardial infarction," Circulation. 116(15):1683-92 (2007).
Segers et al., "Protease-resistant stromal cell-derived factor-1 for the treatment of experimental peripheral artery disease," Circulation. 123(12):1306-15 (2011).
Shioda et al., "Anti-HIV-1 and chemotactic activities of human stromal cell-derived factor 1alpha (SDF-1alpha) and SDF-1beta are abolished by CD26/dipeptidyl peptidase IV-mediated cleavage," Proc Natl Acad Sci U S A. 95(11):6331-6 (1998).
Tan et al., "Cloning and characterizing mutated human stromal cell-derived factor-1 (SDF-1): C-terminal alpha-helix of SDF-1alpha plays a critical role in CXCR4 activation and signaling, but not in CXCR4 binding affinity," Exp Hematol. 34(11):1553-62 (2006).
Valenzuela-Fernandez et al., "Leukocyte elastase negatively regulates Stromal cell-derived factor-1 (SDF-1)/CXCR4 binding and functions by amino-terminal processing of SDF-1 and CXCR4," J Biol Chem. 277(18):15677-89 (2002).
Wang et al., "Roles of chemokine CXCL12 and its receptors in ischemic stroke," Curr Drug Targets. 13(2):166-72 (2012).
Yamaguchi et al., "Stromal cell-derived factor-1 effects on ex vivo expanded endothelial progenitor cell recruitment for ischemic neovascularization," Circulation. 107(9):1322-8 (2003).
Yu et al., "Identification and expression of novel isoforms of human stromal cell-derived factor 1," Gene. 374:174-9 (2006).
Zahradka et al., "Activation of MMP-2 in response to vascular injury is mediated by phosphatidylinositol 3-kinase-dependent expression of MT1-MMP," Am J Physiol Heart Circ Physiol. 287(6):H2861-70 (2004).
Zhang et al., "Controlled release of stromal cell-derived factor-1 alpha in situ increases c-kit+ cell homing to the infarcted heart," Tissue Eng. 13(8):2063-71 (2007).
Zhong et al., "Small peptide analogs to stromal derived factor-1 enhance chemotactic migration of human and mouse hematopoietic cells," Exp Hematol. 32(5):470-5 (2004).
Zou et al., "Function of the chemokine receptor CXCR4 in haematopoiesis and in cerebellar development," Nature. 393(6685):595-9 (1998).
Extended European Search Report for European Patent Application No. 13185216.2, dated Nov. 27, 2013 (13 pages).
Extended European Search Report for European Patent Application No. 07867257.3, dated Aug. 10, 2010 (11 pages).
International Search Report and Written Opinion for International Patent Application No. PCT/US2007/022394, dated Sep. 26, 2008 (14 pages).
International Search Report and Written Opinion for International Patent Application No. PCT/US11/25239, dated Aug. 1, 2011 (13 pages).
International Search Report and Written Opinion for International Patent Application No. PCT/US11/48097, dated Jan. 11, 2012 (17 pages).
International Search Report and Written Opinion for International Patent Application No. PCT/US2012/041054, dated Sep. 17, 2012 (14 pages).
English Translation of Notice of Reasons for Rejection for Japanese Patent Application No. 2014-205586, dated Nov. 9, 2015 (3 pages).
International Search Report and Written Opinion for International Patent Application No. PCT/US2014/070010, dated Apr. 7, 2015 (14 pages).
Notice of Reasons for Rejection for Japanese Patent Application No. 2014-514581, dated Nov. 30, 2015 (8 pages).
Zhang et al., "SDF-1 expression by mesenchymal stem cells results in trophic support of cardiac myocytes after myocardial infarction," FASEB J. 21(12):3197-207 (2007).
Extended European Search Report for European Patent Application No. 14869229.6, dated Apr. 20, 2017 (7 pages).
Claims for U.S. Appl. No. 15/103,153, filed Oct. 13, 2016 (4 pages).
Claims for U.S. Appl. No. 15/374,539, filed Feb. 16, 2017 (4 pages).
Claims for U.S. Appl. No. 14/124,187, filed May 3, 2017 (3 pages).
Office Action for U.S. Appl. No. 15/054,456, dated Aug. 17, 2017 (12 pages).
Office Action for U.S. Appl. No. 15/054,456, dated Feb. 13, 2018 (11 pages).
Office Action for U.S. Appl. No. 15/103,153, dated Jan. 16, 2018 (15 pages).
Ratajczak et al., "The pleiotropic effects of the SDF-1-CXCR4 axis in organogenesis, regeneration and tumorigenesis," Leukemia. 20(11):1915-1924 (2006).
Search Report for Singaporean Patent Application No. 11201604793Y, dated Aug. 7, 2017 (3 pages).
Written Opinion for Singaporean Patent Application No. 11201604793Y, dated Aug. 10, 2017 (7 pages).
Ceradini et al., "Progenitor cell trafficking is regulated by hypoxic gradients through HIF-1 induction of SDF-1," Nat Med. 10(8):858-864 (2004).
Elmadbouh et al., "Ex-vivo delivered stromal cell-derived factor-1alpha promotes stem cell homing and induces angiomyogenesis in the infarcted myocardium," available in PMC Sep. 28, 2009, published in final edited form as: J Mol Cell Cardiol 42(4):792-803 (2007) (19 pages).
Jin et al., "Stromal cell derived factor-1 enhances bone marrow mononuclear cell migration in mice with acute liver failure," World J Gastroenterol 15(21):2657-64 (2009).

* cited by examiner

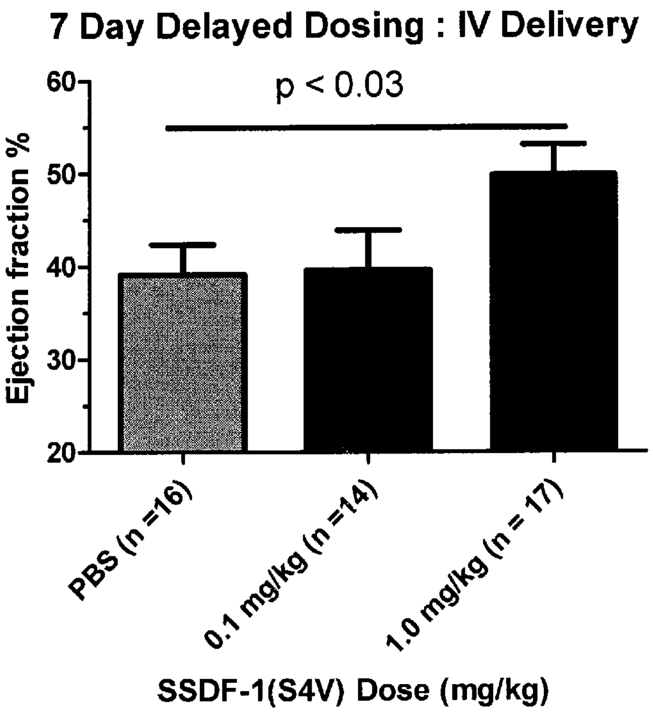
7 Day Delayed Dosing : IV Delivery
p < 0.03
Ejection fraction %
60
50
40
30
20
PBS (n =16)
0.1 mg/kg (n =14)
1.0 mg/kg (n = 17)
SSDF-1(S4V) Dose (mg/kg)

SEQUENCE LISTING

<160> NUMBER OF SEQ ID NOS: 77

<210> SEQ ID NO 1

<400> SEQUENCE: 1

000

<210> SEQ ID NO 2

<400> SEQUENCE: 2

000

<210> SEQ ID NO 3

<400> SEQUENCE: 3

000

<210> SEQ ID NO 4

<400> SEQUENCE: 4

000

-continued

<210> SEQ ID NO 5

<400> SEQUENCE: 5

000

<210> SEQ ID NO 6

<400> SEQUENCE: 6

000

<210> SEQ ID NO 7

<400> SEQUENCE: 7

000

<210> SEQ ID NO 8

<400> SEQUENCE: 8

000

<210> SEQ ID NO 9

<400> SEQUENCE: 9

000

<210> SEQ ID NO 10

<400> SEQUENCE: 10

000

<210> SEQ ID NO 11

<400> SEQUENCE: 11

000

<210> SEQ ID NO 12

<400> SEQUENCE: 12

000

<210> SEQ ID NO 13

<400> SEQUENCE: 13

000

<210> SEQ ID NO 14

<400> SEQUENCE: 14

000

<210> SEQ ID NO 15

<400> SEQUENCE: 15

000

-continued

<210> SEQ ID NO 16

<400> SEQUENCE: 16

000

<210> SEQ ID NO 17

<400> SEQUENCE: 17

000

<210> SEQ ID NO 18

<400> SEQUENCE: 18

000

<210> SEQ ID NO 19

<400> SEQUENCE: 19

000

<210> SEQ ID NO 20

<400> SEQUENCE: 20

000

<210> SEQ ID NO 21

<400> SEQUENCE: 21

000

<210> SEQ ID NO 22

<400> SEQUENCE: 22

000

<210> SEQ ID NO 23

<400> SEQUENCE: 23

000

<210> SEQ ID NO 24

<400> SEQUENCE: 24

000

<210> SEQ ID NO 25

<400> SEQUENCE: 25

000

<210> SEQ ID NO 26

<400> SEQUENCE: 26

000

-continued

<210> SEQ ID NO 27

<400> SEQUENCE: 27

000

<210> SEQ ID NO 28

<400> SEQUENCE: 28

000

<210> SEQ ID NO 29

<400> SEQUENCE: 29

000

<210> SEQ ID NO 30

<400> SEQUENCE: 30

000

<210> SEQ ID NO 31

<400> SEQUENCE: 31

000

<210> SEQ ID NO 32

<400> SEQUENCE: 32

000

<210> SEQ ID NO 33

<400> SEQUENCE: 33

000

<210> SEQ ID NO 34

<400> SEQUENCE: 34

000

<210> SEQ ID NO 35

<400> SEQUENCE: 35

000

<210> SEQ ID NO 36

<400> SEQUENCE: 36

000

<210> SEQ ID NO 37

<400> SEQUENCE: 37

000

-continued

<210> SEQ ID NO 38

<400> SEQUENCE: 38

000

<210> SEQ ID NO 39

<400> SEQUENCE: 39

000

<210> SEQ ID NO 40

<400> SEQUENCE: 40

000

<210> SEQ ID NO 41

<400> SEQUENCE: 41

000

<210> SEQ ID NO 42

<400> SEQUENCE: 42

000

<210> SEQ ID NO 43

<400> SEQUENCE: 43

000

<210> SEQ ID NO 44

<400> SEQUENCE: 44

000

<210> SEQ ID NO 45

<400> SEQUENCE: 45

000

<210> SEQ ID NO 46

<400> SEQUENCE: 46

000

<210> SEQ ID NO 47

<400> SEQUENCE: 47

000

<210> SEQ ID NO 48

<400> SEQUENCE: 48

000

<210> SEQ ID NO 49

<400> SEQUENCE: 49

000

<210> SEQ ID NO 50

<400> SEQUENCE: 50

000

<210> SEQ ID NO 51

<400> SEQUENCE: 51

000

<210> SEQ ID NO 52
<211> LENGTH: 68
<212> TYPE: PRT
<213> ORGANISM: Homo sapiens

<400> SEQUENCE: 52

```
Lys Pro Val Ser Leu Ser Tyr Arg Cys Pro Cys Arg Phe Phe Glu Ser
1               5                   10                  15

His Val Ala Arg Ala Asn Val Lys His Leu Lys Ile Leu Asn Thr Pro
            20                  25                  30

Asn Cys Ala Leu Gln Ile Val Ala Arg Leu Lys Asn Asn Asn Arg Gln
        35                  40                  45

Val Cys Ile Asp Pro Lys Leu Lys Trp Ile Gln Glu Tyr Leu Glu Lys
    50                  55                  60

Ala Leu Asn Lys
65
```

<210> SEQ ID NO 53
<211> LENGTH: 68
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(6)

<400> SEQUENCE: 53

```
Lys Pro Xaa Xaa Xaa Xaa Tyr Arg Cys Pro Cys Arg Phe Phe Glu Ser
1               5                   10                  15

His Val Ala Arg Ala Asn Val Lys His Leu Lys Ile Leu Asn Thr Pro
            20                  25                  30

Asn Cys Ala Leu Gln Ile Val Ala Arg Leu Lys Asn Asn Asn Arg Gln
        35                  40                  45

Val Cys Ile Asp Pro Lys Leu Lys Trp Ile Gln Glu Tyr Leu Glu Lys
    50                  55                  60

Ala Leu Asn Lys
65
```

<210> SEQ ID NO 54
<211> LENGTH: 68
<212> TYPE: PRT
<213> ORGANISM: Artificial Sequence
<220> FEATURE:
<223> OTHER INFORMATION: Synthetic Construct

<400> SEQUENCE: 54

Lys Pro His Ser Leu Ser Tyr Arg Cys Pro Cys Arg Phe Phe Glu Ser
1               5                   10                  15

His Val Ala Arg Ala Asn Val Lys His Leu Lys Ile Leu Asn Thr Pro
            20                  25                  30

Asn Cys Ala Leu Gln Ile Val Ala Arg Leu Lys Asn Asn Asn Arg Gln
        35                  40                  45

Val Cys Ile Asp Pro Lys Leu Lys Trp Ile Gln Glu Tyr Leu Glu Lys
    50                  55                  60

Ala Leu Asn Lys
65

<210> SEQ ID NO 55
<211> LENGTH: 68
<212> TYPE: PRT
<213> ORGANISM: Artificial Sequence
<220> FEATURE:
<223> OTHER INFORMATION: Synthetic Construct

<400> SEQUENCE: 55

Lys Pro Cys Ser Leu Ser Tyr Arg Cys Pro Cys Arg Phe Phe Glu Ser
1               5                   10                  15

His Val Ala Arg Ala Asn Val Lys His Leu Lys Ile Leu Asn Thr Pro
            20                  25                  30

Asn Cys Ala Leu Gln Ile Val Ala Arg Leu Lys Asn Asn Asn Arg Gln
        35                  40                  45

Val Cys Ile Asp Pro Lys Leu Lys Trp Ile Gln Glu Tyr Leu Glu Lys
    50                  55                  60

Ala Leu Asn Lys
65

<210> SEQ ID NO 56
<211> LENGTH: 68
<212> TYPE: PRT
<213> ORGANISM: Artificial Sequence
<220> FEATURE:
<223> OTHER INFORMATION: Synthetic Construct

<400> SEQUENCE: 56

Lys Pro Val Ser Thr Ser Tyr Arg Cys Pro Cys Arg Phe Phe Glu Ser
1               5                   10                  15

His Val Ala Arg Ala Asn Val Lys His Leu Lys Ile Leu Asn Thr Pro
            20                  25                  30

Asn Cys Ala Leu Gln Ile Val Ala Arg Leu Lys Asn Asn Asn Arg Gln
        35                  40                  45

Val Cys Ile Asp Pro Lys Leu Lys Trp Ile Gln Glu Tyr Leu Glu Lys
    50                  55                  60

Ala Leu Asn Lys
65

<210> SEQ ID NO 57

<400> SEQUENCE: 57

000

<210> SEQ ID NO 58

<400> SEQUENCE: 58

000

<210> SEQ ID NO 59

<400> SEQUENCE: 59

000

<210> SEQ ID NO 60
<211> LENGTH: 68
<212> TYPE: PRT
<213> ORGANISM: Artificial Sequence
<220> FEATURE:
<223> OTHER INFORMATION: Synthetic Construct

<400> SEQUENCE: 60

```
Lys Pro Val Ser Val Ser Tyr Arg Cys Pro Cys Arg Phe Phe Glu Ser
1               5                   10                  15

His Val Ala Arg Ala Asn Val Lys His Leu Lys Ile Leu Asn Thr Pro
            20                  25                  30

Asn Cys Ala Leu Gln Ile Val Ala Arg Leu Lys Asn Asn Asn Arg Gln
        35                  40                  45

Val Cys Ile Asp Pro Lys Leu Lys Trp Ile Gln Glu Tyr Leu Glu Lys
    50                  55                  60

Ala Leu Asn Lys
65
```

<210> SEQ ID NO 61
<211> LENGTH: 68
<212> TYPE: PRT
<213> ORGANISM: Artificial Sequence
<220> FEATURE:
<223> OTHER INFORMATION: Synthetic Construct

<400> SEQUENCE: 61

```
Lys Pro Val Ser Leu Cys Tyr Arg Cys Pro Cys Arg Phe Phe Glu Ser
1               5                   10                  15

His Val Ala Arg Ala Asn Val Lys His Leu Lys Ile Leu Asn Thr Pro
            20                  25                  30

Asn Cys Ala Leu Gln Ile Val Ala Arg Leu Lys Asn Asn Asn Arg Gln
        35                  40                  45

Val Cys Ile Asp Pro Lys Leu Lys Trp Ile Gln Glu Tyr Leu Glu Lys
    50                  55                  60

Ala Leu Asn Lys
65
```

<210> SEQ ID NO 62
<211> LENGTH: 68
<212> TYPE: PRT
<213> ORGANISM: Artificial Sequence
<220> FEATURE:
<223> OTHER INFORMATION: Synthetic Construct

<400> SEQUENCE: 62

```
Lys Pro Val Ser Leu Gly Tyr Arg Cys Pro Cys Arg Phe Phe Glu Ser
1               5                   10                  15

His Val Ala Arg Ala Asn Val Lys His Leu Lys Ile Leu Asn Thr Pro
            20                  25                  30
```

-continued

```
Asn Cys Ala Leu Gln Ile Val Ala Arg Leu Lys Asn Asn Asn Arg Gln
        35                  40                  45

Val Cys Ile Asp Pro Lys Leu Lys Trp Ile Gln Glu Tyr Leu Glu Lys
    50                  55                  60

Ala Leu Asn Lys
65


<210> SEQ ID NO 63
<211> LENGTH: 68
<212> TYPE: PRT
<213> ORGANISM: Artificial Sequence
<220> FEATURE:
<223> OTHER INFORMATION: Synthetic Construct

<400> SEQUENCE: 63

Lys Pro Val Val Leu Ser Tyr Arg Cys Pro Cys Arg Phe Phe Glu Ser
1               5                   10                  15

His Val Ala Arg Ala Asn Val Lys His Leu Lys Ile Leu Asn Thr Pro
            20                  25                  30

Asn Cys Ala Leu Gln Ile Val Ala Arg Leu Lys Asn Asn Asn Arg Gln
        35                  40                  45

Val Cys Ile Asp Pro Lys Leu Lys Trp Ile Gln Glu Tyr Leu Glu Lys
    50                  55                  60

Ala Leu Asn Lys
65


<210> SEQ ID NO 64
<211> LENGTH: 68
<212> TYPE: PRT
<213> ORGANISM: Artificial Sequence
<220> FEATURE:
<223> OTHER INFORMATION: Synthetic Construct

<400> SEQUENCE: 64

Lys Pro Val Ser Pro Ser Tyr Arg Cys Pro Cys Arg Phe Phe Glu Ser
1               5                   10                  15

His Val Ala Arg Ala Asn Val Lys His Leu Lys Ile Leu Asn Thr Pro
            20                  25                  30

Asn Cys Ala Leu Gln Ile Val Ala Arg Leu Lys Asn Asn Asn Arg Gln
        35                  40                  45

Val Cys Ile Asp Pro Lys Leu Lys Trp Ile Gln Glu Tyr Leu Glu Lys
    50                  55                  60

Ala Leu Asn Lys
65


<210> SEQ ID NO 65
<211> LENGTH: 68
<212> TYPE: PRT
<213> ORGANISM: Artificial Sequence
<220> FEATURE:
<223> OTHER INFORMATION: Synthetic Construct

<400> SEQUENCE: 65

Lys Pro Val Val Pro Ser Tyr Arg Cys Pro Cys Arg Phe Phe Glu Ser
1               5                   10                  15

His Val Ala Arg Ala Asn Val Lys His Leu Lys Ile Leu Asn Thr Pro
            20                  25                  30

Asn Cys Ala Leu Gln Ile Val Ala Arg Leu Lys Asn Asn Asn Arg Gln
        35                  40                  45
```

-continued

```
Val Cys Ile Asp Pro Lys Leu Lys Trp Ile Gln Glu Tyr Leu Glu Lys
    50                  55                  60

Ala Leu Asn Lys
65


<210> SEQ ID NO 66
<211> LENGTH: 5
<212> TYPE: PRT
<213> ORGANISM: Artificial Sequence
<220> FEATURE:
<223> OTHER INFORMATION: Synthetic Construct

<400> SEQUENCE: 66

Gly Gly Gly Gly Ser
1               5


<210> SEQ ID NO 67
<211> LENGTH: 302
<212> TYPE: PRT
<213> ORGANISM: Artificial Sequence
<220> FEATURE:
<223> OTHER INFORMATION: Synthetic Construct

<400> SEQUENCE: 67

Ser Lys Pro Val Val Leu Ser Tyr Arg Cys Pro Cys Arg Phe Phe Glu
1               5                   10                  15

Ser His Val Ala Arg Ala Asn Val Lys His Leu Lys Ile Leu Asn Thr
            20                  25                  30

Pro Asn Cys Ala Leu Gln Ile Val Ala Arg Leu Lys Asn Asn Asn Arg
        35                  40                  45

Gln Val Cys Ile Asp Pro Lys Leu Lys Trp Ile Gln Glu Tyr Leu Glu
    50                  55                  60

Lys Ala Leu Asn Lys Gly Gly Gly Gly Ser Val Asp Lys Thr His Thr
65                  70                  75                  80

Cys Pro Pro Cys Pro Ala Pro Glu Leu Leu Gly Gly Pro Ser Val Phe
                85                  90                  95

Leu Phe Pro Pro Lys Pro Lys Asp Thr Leu Met Ile Ser Arg Thr Pro
            100                 105                 110

Glu Val Thr Cys Val Val Val Asp Val Ser His Glu Asp Pro Glu Val
        115                 120                 125

Lys Phe Asn Trp Tyr Val Asp Gly Val Glu Val His Asn Ala Lys Thr
    130                 135                 140

Lys Pro Arg Glu Glu Gln Tyr Asn Ser Thr Tyr Arg Val Val Ser Val
145                 150                 155                 160

Leu Thr Val Leu His Gln Asp Trp Leu Asn Gly Lys Glu Tyr Lys Cys
                165                 170                 175

Lys Val Ser Asn Lys Ala Leu Pro Ala Pro Ile Glu Lys Thr Ile Ser
            180                 185                 190

Lys Ala Lys Gly Gln Pro Arg Glu Pro Gln Val Tyr Thr Leu Pro Pro
        195                 200                 205

Ser Arg Asp Glu Leu Thr Lys Asn Gln Val Ser Leu Thr Cys Leu Val
    210                 215                 220

Lys Gly Phe Tyr Pro Ser Asp Ile Ala Val Glu Trp Glu Ser Asn Gly
225                 230                 235                 240

Gln Pro Glu Asn Asn Tyr Lys Thr Thr Pro Pro Val Leu Asp Ser Asp
                245                 250                 255

Gly Ser Phe Phe Leu Tyr Ser Lys Leu Thr Val Asp Lys Ser Arg Trp
            260                 265                 270
```

-continued

```
Gln Gln Gly Asn Val Phe Ser Cys Ser Val Met His Glu Ala Leu His
        275                 280                 285

Asn His Tyr Thr Gln Lys Ser Leu Ser Leu Ser Pro Gly Lys
    290                 295                 300


<210> SEQ ID NO 68
<211> LENGTH: 69
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(7)

<400> SEQUENCE: 68

Ser Lys Pro Xaa Xaa Xaa Xaa Tyr Arg Cys Pro Cys Arg Phe Phe Glu
1               5                   10                  15

Ser His Val Ala Arg Ala Asn Val Lys His Leu Lys Ile Leu Asn Thr
            20                  25                  30

Pro Asn Cys Ala Leu Gln Ile Val Ala Arg Leu Lys Asn Asn Asn Arg
        35                  40                  45

Gln Val Cys Ile Asp Pro Lys Leu Lys Trp Ile Gln Glu Tyr Leu Glu
    50                  55                  60

Lys Ala Leu Asn Lys
65


<210> SEQ ID NO 69
<211> LENGTH: 69
<212> TYPE: PRT
<213> ORGANISM: Artificial Sequence
<220> FEATURE:
<223> OTHER INFORMATION: Synthetic Construct

<400> SEQUENCE: 69

Ser Lys Pro Val Val Leu Ser Tyr Arg Cys Pro Cys Arg Phe Phe Glu
1               5                   10                  15

Ser His Val Ala Arg Ala Asn Val Lys His Leu Lys Ile Leu Asn Thr
            20                  25                  30

Pro Asn Cys Ala Leu Gln Ile Val Ala Arg Leu Lys Asn Asn Asn Arg
        35                  40                  45

Gln Val Cys Ile Asp Pro Lys Leu Lys Trp Ile Gln Glu Tyr Leu Glu
    50                  55                  60

Lys Ala Leu Asn Lys
65


<210> SEQ ID NO 70
<211> LENGTH: 69
<212> TYPE: PRT
<213> ORGANISM: Artificial Sequence
<220> FEATURE:
<223> OTHER INFORMATION: Synthetic Construct

<400> SEQUENCE: 70

Ser Lys Pro Val Ser Pro Ser Tyr Arg Cys Pro Cys Arg Phe Phe Glu
1               5                   10                  15

Ser His Val Ala Arg Ala Asn Val Lys His Leu Lys Ile Leu Asn Thr
            20                  25                  30

Pro Asn Cys Ala Leu Gln Ile Val Ala Arg Leu Lys Asn Asn Asn Arg
        35                  40                  45
```

Gln Val Cys Ile Asp Pro Lys Leu Lys Trp Ile Gln Glu Tyr Leu Glu
    50                  55                  60

Lys Ala Leu Asn Lys
65

<210> SEQ ID NO 71
<211> LENGTH: 69
<212> TYPE: PRT
<213> ORGANISM: Artificial Sequence
<220> FEATURE:
<223> OTHER INFORMATION: Synthetic Construct

<400> SEQUENCE: 71

Ser Lys Pro Val Val Pro Ser Tyr Arg Cys Pro Cys Arg Phe Phe Glu
1               5                   10                  15

Ser His Val Ala Arg Ala Asn Val Lys His Leu Lys Ile Leu Asn Thr
            20                  25                  30

Pro Asn Cys Ala Leu Gln Ile Val Ala Arg Leu Lys Asn Asn Asn Arg
        35                  40                  45

Gln Val Cys Ile Asp Pro Lys Leu Lys Trp Ile Gln Glu Tyr Leu Glu
    50                  55                  60

Lys Ala Leu Asn Lys
65

<210> SEQ ID NO 72
<211> LENGTH: 69
<212> TYPE: PRT
<213> ORGANISM: Artificial Sequence
<220> FEATURE:
<223> OTHER INFORMATION: Synthetic Construct

<400> SEQUENCE: 72

Ser Lys Pro His Ser Leu Ser Tyr Arg Cys Pro Cys Arg Phe Phe Glu
1               5                   10                  15

Ser His Val Ala Arg Ala Asn Val Lys His Leu Lys Ile Leu Asn Thr
            20                  25                  30

Pro Asn Cys Ala Leu Gln Ile Val Ala Arg Leu Lys Asn Asn Asn Arg
        35                  40                  45

Gln Val Cys Ile Asp Pro Lys Leu Lys Trp Ile Gln Glu Tyr Leu Glu
    50                  55                  60

Lys Ala Leu Asn Lys
65

<210> SEQ ID NO 73
<211> LENGTH: 69
<212> TYPE: PRT
<213> ORGANISM: Artificial Sequence
<220> FEATURE:
<223> OTHER INFORMATION: Synthetic Construct

<400> SEQUENCE: 73

Ser Lys Pro Cys Ser Leu Ser Tyr Arg Cys Pro Cys Arg Phe Phe Glu
1               5                   10                  15

Ser His Val Ala Arg Ala Asn Val Lys His Leu Lys Ile Leu Asn Thr
            20                  25                  30

Pro Asn Cys Ala Leu Gln Ile Val Ala Arg Leu Lys Asn Asn Asn Arg
        35                  40                  45

-continued

```
Gln Val Cys Ile Asp Pro Lys Leu Lys Trp Ile Gln Glu Tyr Leu Glu
    50                  55                  60

Lys Ala Leu Asn Lys
65


<210> SEQ ID NO 74
<211> LENGTH: 69
<212> TYPE: PRT
<213> ORGANISM: Artificial Sequence
<220> FEATURE:
<223> OTHER INFORMATION: Synthetic Construct

<400> SEQUENCE: 74

Ser Lys Pro Val Ser Thr Ser Tyr Arg Cys Pro Cys Arg Phe Phe Glu
1               5                   10                  15

Ser His Val Ala Arg Ala Asn Val Lys His Leu Lys Ile Leu Asn Thr
            20                  25                  30

Pro Asn Cys Ala Leu Gln Ile Val Ala Arg Leu Lys Asn Asn Asn Arg
        35                  40                  45

Gln Val Cys Ile Asp Pro Lys Leu Lys Trp Ile Gln Glu Tyr Leu Glu
    50                  55                  60

Lys Ala Leu Asn Lys
65


<210> SEQ ID NO 75
<211> LENGTH: 69
<212> TYPE: PRT
<213> ORGANISM: Artificial Sequence
<220> FEATURE:
<223> OTHER INFORMATION: Synthetic Construct

<400> SEQUENCE: 75

Ser Lys Pro Val Ser Val Ser Tyr Arg Cys Pro Cys Arg Phe Phe Glu
1               5                   10                  15

Ser His Val Ala Arg Ala Asn Val Lys His Leu Lys Ile Leu Asn Thr
            20                  25                  30

Pro Asn Cys Ala Leu Gln Ile Val Ala Arg Leu Lys Asn Asn Asn Arg
        35                  40                  45

Gln Val Cys Ile Asp Pro Lys Leu Lys Trp Ile Gln Glu Tyr Leu Glu
    50                  55                  60

Lys Ala Leu Asn Lys
65


<210> SEQ ID NO 76
<211> LENGTH: 69
<212> TYPE: PRT
<213> ORGANISM: Artificial Sequence
<220> FEATURE:
<223> OTHER INFORMATION: Synthetic Construct

<400> SEQUENCE: 76

Ser Lys Pro Val Ser Leu Cys Tyr Arg Cys Pro Cys Arg Phe Phe Glu
1               5                   10                  15

Ser His Val Ala Arg Ala Asn Val Lys His Leu Lys Ile Leu Asn Thr
            20                  25                  30

Pro Asn Cys Ala Leu Gln Ile Val Ala Arg Leu Lys Asn Asn Asn Arg
        35                  40                  45
```

-continued

```
Gln Val Cys Ile Asp Pro Lys Leu Lys Trp Ile Gln Glu Tyr Leu Glu
    50                  55                  60

Lys Ala Leu Asn Lys
65


<210> SEQ ID NO 77
<211> LENGTH: 69
<212> TYPE: PRT
<213> ORGANISM: Artificial Sequence
<220> FEATURE:
<223> OTHER INFORMATION: Synthetic Construct

<400> SEQUENCE: 77

Ser Lys Pro Val Ser Leu Gly Tyr Arg Cys Pro Cys Arg Phe Phe Glu
1               5                   10                  15

Ser His Val Ala Arg Ala Asn Val Lys His Leu Lys Ile Leu Asn Thr
            20                  25                  30

Pro Asn Cys Ala Leu Gln Ile Val Ala Arg Leu Lys Asn Asn Asn Arg
        35                  40                  45

Gln Val Cys Ile Asp Pro Lys Leu Lys Trp Ile Gln Glu Tyr Leu Glu
    50                  55                  60

Lys Ala Leu Asn Lys
65
```

METHODS FOR REPAIRING TISSUE DAMAGE USING PROTEASE-RESISTANT MUTANTS OF STROMAL CELL DERIVED FACTOR-1

CROSS-REFERENCE TO RELATED APPLICATION

This application is the U.S. national stage filing under 35 U.S.C. § 371 of International Application No. PCT/US2012/041054, filed Jun. 6, 2012, which claims the benefit of the filing date of U.S. Provisional Patent Application No. 61/494,079, filed Jun. 7, 2011.

BACKGROUND OF THE INVENTION

In general, the invention relates to methods of repairing tissue damage using SDF-1 or protease-resistant mutants of stromal cell derived factor-1 (SDF-1).

SDF-1 (also known as CXCL12) is a 68 amino acid member of the chemokine family that is a chemoattractant for resting T-lymphocytes, monocytes, and $CD34^+$ stem cells. SDF-1 is produced in multiple forms: SDF-1α (CXCL12a), SDF-1β (CXCL12b), and SDF-1γ, which are the result of differential mRNA splicing. The sequences of SDF-1α and SDF-1β are essentially the same, except that SDF-1β is extended by four amino acids (Arg-Phe-Lys-Met) at the C-terminus. The first three exons of SDF-1γ are identical to those of SDF-1α and SDF-1β. The fourth exon of SDF-1γ is located 3200 base-pairs downstream from the third exon on the SDF-1 locus and lies between the third exon and the fourth exon of SDF-1β. SDF-1 is initially made with a signal peptide (21 amino acids in length) that is cleaved to make the active peptide.

SDF-1 plays a key role in the homing of hematopoietic stem cells to bone marrow during embryonic development and after stem cell transplantation. In addition to its role in stem cell homing, SDF-1 is also important in cardiogenesis and vasculogenesis. SDF-1-deficient mice die perinatally and have defects in cardiac ventricular septal formation, bone marrow hematopoiesis, and organ-specific vasculogenesis. It has also been reported that abnormally low levels of SDF-1 are at least partially responsible for impaired wound healing associated with diabetic patients and that impairment can be reversed by the administration of SDF-1 at the site of tissue damage.

In the normal adult heart, SDF-1 is expressed constitutively, but expression is upregulated within days after myocardial infarction. It has been shown previously that SDF-1 expression increased eight weeks after myocardial infarction by intramyocardial transplantation of stably transfected cardiac fibroblasts overexpressing SDF-1, in combination with G-CSF therapy. This procedure was associated with higher numbers of bone marrow stem cells (c-Kit or $CD34^+$) and endothelial cells in the heart and resulted in an increase of vascular density and an improvement of left ventricular function. These studies suggest that the insufficiency of the naturally-occurring myocardial repair process may be, in part, due to inadequate SDF-1 availability. Hence, the delivery of SDF-1 in a controlled manner after myocardial infarction may attract more progenitor cells and thereby promote tissue repair.

There exists a need in the art for improved methods of promoting wound healing and tissue repair.

SUMMARY OF THE INVENTION

SDF-1 is involved in the homing of hematopoietic stem cells and in cardiogenesis and vasculogenesis. In order to promote its stem cell recruitment and wound healing effects, a local gradient of SDF-1 is believed to be required to attract progenitors and to promote revascularization and repair. We have discovered that systemic delivery, and specifically intravenous (“TV”) delivery, of SDF-1 and protease resistant SDF-1 mutants is very effective for the treatment of tissue damage, a surprising result given the requirement for a local gradient of SDF-1. IV delivery has many clinical advantages compared to other routes of administration, including but not limited to ease of delivery. In addition, we have discovered that a delay in dosing of anywhere from several minutes post tissue damage event (e.g., myocardial infarction) up to several hours, several days, several weeks, or several months after the onset of tissue damage (e.g. cardiac tissue damage, vascular tissue damage, or tissue damage from wounds) of the intravenous administration of the SDF-1 or mutant SDF-1 peptides is also effective for promoting revascularization and repair. Here again, our discovery of the efficacy of the compositions after a period of delay is an unexpected finding given the acute nature of the tissue damage in some conditions and diseases.

Accordingly, the present invention features the intravenous administration of compositions that include SDF-1 and mutant SDF-1 peptides that have been mutated in a manner that preserves their ability to function as chemoattractants, but renders them resistant to inactivation by proteases, particularly matrix metalloproteinase-2 (MMP-2), matrix metalloproteinase-9 (MMP-9), dipeptidyl peptidase IV (DPPIV/CD26), leukocyte elastase, cathepsin G, carboxypeptidase M, and carboxypeptidase N. The methods of the present invention may be useful in the treatment of, for example, peripheral vascular disease (PVD; also known as peripheral artery disease (PAD) or peripheral artery occlusive disease (PAOD)); ulcers in the gastrointestinal tract or elsewhere; wounds resulting from accident, surgery, or disease; chronic heart failure; tissue damage; or cardiac tissue damaged as a result of myocardial infarction or other cardiovascular event. The methods of the present invention may also be useful in treating or reducing the likelihood of tissue damage caused by wounds, ulcers, or lesions in diabetic patients.

In one aspect, the invention features a method of treating or ameliorating tissue damage (e.g., tissue damage resulting from a disease or condition) in a subject in need thereof by intravenously administering a composition that includes an isolated SDF-1 or mutant form of SDF-1 peptide with the formula of: a mutant SDF-1 (mSDF-1), mSDF-1-$Y_z$, $X_p$-mSDF-1, or $X_p$-mSDF-1-$Y_z$. SDF-1 is a peptide with the amino acid sequence of at least amino acids 1-8 of SEQ ID NO:53 and which may be optionally extended at the C-terminus by all or any portion of the remaining sequence of SEQ ID NO:53, and SEQ ID NO:53 includes the amino acid sequence:

(SEQ ID NO: 53)

K P $X_3$ $X_4$ $X_5$ $X_6$ Y R C P C R F F E S H V A R A N V K H L K I L N T P N C A L Q I V A R L K N N N R Q V C I D P K L K W I Q E Y L E K A L N K, wherein $X_3$, $X_4$, $X_5$, and $X_6$ are any amino acid, and a) $X_p$ is a proteinogenic amino acid(s) or a protease protective organic group and p is any integer from 1 to 4;

b) $Y_z$ is a proteinogenic amino acid(s) or protease protective organic group and z is any integer from 1 to 4;

c) mSDF-1 or mSDF-1-$Y_z$ maintains chemoattractant activity for T cells and is inactivated by matrix metalloproteinase-2 (MMP-2), matrix metalloproteinase-9 (MMP-9), leukocyte elastase, and/or cathepsin G at a rate that is at least 50% less than the rate of inactivation of native SDF-1; and d) $X_p$-mSDF-1 or $X_p$-mSDF-1-$Y_z$ maintains chemoattractant activity for T cells, is inactivated by dipeptidyl peptidase IV (DPPIV) at a rate that is at least 50% less than the rate at which native SDF-1 is inactivated, and is inactivated by MMP-2, MMP-9, leukocyte elastase, and/or cathepsin G at a rate that is at least 50% less than the rate of inactivation of native SDF-1;

wherein isolated mutant form of SDF-1 is administered intravenously in an amount sufficient to treat or ameliorate tissue damage in a subject.

In one particular embodiment, the isolated mutant form of SDF-1 peptide does not include the amino acid sequence of at least amino acids 1-8 of SEQ ID NO:52.

In one embodiment, $X_3$ is valine, histidine, or cysteine. In another embodiment, $X_4$ is serine or valine. In another embodiment, $X_5$ is leucine, proline, threonine, or valine. In another embodiment, $X_6$ is serine, cysteine, or glycine.

In certain embodiments of the methods of the present invention, the peptide is an $X_p$-mSDF-1 peptide or $X_p$-mSDF-1-$Y_z$, peptide, wherein X is a serine and p is 1. In other embodiments, the peptide is an mSDF-1-$Y_z$ peptide or $X_p$-mSDF-1-$Y_z$ peptide, wherein Y is a serine and z is 1.

In certain embodiments, C-terminal modifications, including the addition of an Fc peptide may be made to any of the SDF-I peptides described herein including, but not limited to, wild-type SDF-1.

In certain embodiments, the isolated mutant form of SDF-1 includes the sequence set forth in SEQ ID NOs: 63, 67, or 69.

The methods of the present invention may also feature an isolated mutant form of SDF-1, wherein SDF-1 is a fusion protein with the formula A-$(L)_n$-Fc, wherein: A is the isolated mutant form of SDF-1; n is an integer from 0-3 (e.g., 1); L is a linker sequence of 3-9 amino acids; and Fc is an Fc peptide from an Fc region of an immunoglobulin. In certain embodiments, L is GGGGS (SEQ ID NO:66). In certain embodiments, the fusion protein may form a biologically compatible peptide membrane.

In any embodiment of the present invention, the disease or condition being treated may be stroke, limb isehemia, tissue damage due to trauma, myocardial infarction, peripheral vascular disease, chronic heart failure, or diabetes.

In any embodiment of the present invention, the damaged tissue is a cardiac tissue or a vascular tissue.

In any embodiment of the present invention, the SDF-1 or mutant SDF-1 protein composition is administered to any vein in the body of a mammal, including but not limited to a peripheral vein (e.g., a vein on the arm, a vein in the leg, the back of the hand, or the median cubital vein) or a central vein, for example, via a central intravenous line to a large vein (e.g., the superior vena cava or inferior vena cava or within the right atrium of the heart).

In any embodiment of the present invention, the SDF-1 or mutant SDF-1 protein composition is administered within minutes, or within 1 hour, 2 hours, 3 hours, 4 hours, 6 hours, 12 hours, 24 hours, at least 48 hours, at least 3 days, 4 days, 5 days, 6 days, 7 days, 10 days, 2 weeks, one month, two months, three months, six months, one year, two years, or more after initial occurrence of the tissue damage or after onset, recognition, or diagnosis of the disease or condition.

In additional embodiments of the present invention, the SDF-1 or mutant SDF-1 protein composition is administered in combination with intra-arterial administration of SDF-1 or a mutant SDF-1 peptide. The intravenous administration can be before or after the intra-arterial administration. In one example, an SDF-1 or mutant SDF-1 protein composition is administered first intra-arterially and then, after a period of time ranging from several minutes to 1 hour to several hours, to 1 day to 1 week to 1 month to 1 year, the SDF-1 or mutant SDF-1 protein composition is administered intravenously. The intra-arterial administration may be repeated during the period of time prior to the intravenous administration or after the intravenous administration.

The SDF-1 or mutant SDF-1 protein composition may be administered one or more times to ameliorate one or more symptoms of the disease or condition. The SDF-1 or mutant SDF-1 composition may be administered one or more times until the tissue damage is reduced, the tissue is repaired, or new blood vessel formation occurs.

In various embodiments, the disease or condition is tissue damage due to trauma, myocardial infarction, or peripheral vascular disease. In additional embodiments, the disease or condition is a cardiovascular disease.

In any embodiment of the present invention, the damaged tissue is a cardiac tissue or a vascular tissue.

By "an amount sufficient" is meant the amount of a therapeutic agent (e.g., an mSDF-1 peptide), alone or in combination with another therapeutic regimen, required to treat or ameliorate a disorder or condition in a clinically relevant manner. In one example, a sufficient amount of an SDF-1 or mutant SDF-1 peptide of the invention is an amount that promotes wound healing or tissue repair or new blood vessel formation (e.g., vasculogenesis). A sufficient amount of a therapeutic agent used to practice the present invention for therapeutic treatment of, e.g., tissue damage varies depending upon the manner of administration, age, and general health of the subject. Ultimately, the medical practitioner prescribing such treatment will decide the appropriate amount and dosage regimen.

By "fragment" is meant a portion of a nucleic acid or polypeptide that contains at least, e.g., 10%, 20%, 30%, 40%, 50%, 60%, 70%, 80%, 90%, 95%, or more of the entire length of the nucleic acid or polypeptide. A nucleic acid fragment may contain, e.g., 10, 20, 30, 40, 50, 60, 70, 80, 90, 100, or 200 or more nucleotides, up to the full length of the nucleic acid. A polypeptide fragment may contain, e.g., 10, 20, 30, 40, 50, or 60 or more amino acids, up to the full length of the polypeptide. Fragments can be modified as described herein and as known in the art.

By "intravenous administration," "intravenous therapy," "IV administration," or "IV therapy" is meant the administration of a substance into a vein (e.g., peripheral or central). Intravenous administration may include direct injection into a vein via a needle connected directly to a syringe or connected to a length of tubing and a container (e.g., a sterile container housing the pharmaceutical composition to be administered).

By "pharmaceutically acceptable carrier" is meant a carrier that is physiologically acceptable to the treated subject while retaining the therapeutic properties of the composition with which it is administered. One exemplary pharmaceutically acceptable carrier substance is physiological saline. Other physiologically acceptable carriers and their formulations are known to one skilled in the art and are described, for example, in Remington's Pharmaceutical Sciences ($20^{th}$ edition, ed. A. Gennaro, 2000, Lippincott, Williams & Wilkins, Philadelphia, Pa.).

By "promoting wound healing" or "promoting tissue repair" is meant augmenting, improving, increasing, or inducing closure, healing, or repair of a wound or damaged tissue. The wound or tissue damage may be the result of any disorder or condition (e.g., disease, injury, or surgery) and may be found in any location in the subject (e.g., an internal or external wound). For example, the wound or tissue damage may be the result of a cardiovascular condition such as, e.g., myocardial infarction, and the damaged tissue may be cardiac tissue. Alternatively, the wound or tissue damage may be the result of peripheral vascular disease or diabetes.

By "protein," "polypeptide," "polypeptide fragment," or "peptide" is meant any chain of two or more amino acid residues, regardless of posttranslational modification (e.g., glycosylation or phosphorylation), constituting all or part of a naturally occurring polypeptide or peptide or constituting a non-naturally occurring polypeptide or peptide. A polypeptide or peptide may be said to be "isolated" or "substantially pure" when physical, mechanical, or chemical methods have been employed to remove the polypeptide from cellular constituents. An "isolated peptide," "substantially pure polypeptide," or "substantially pure and isolated polypeptide" is typically considered removed from cellular constituents and substantially pure when it is at least 60% by weight free from the proteins and naturally occurring organic molecules with which it is naturally associated. The polypeptide may be at least 75%, 80%, 85%, 90%, 95%, or 99% by weight pure. A substantially pure polypeptide may be obtained by standard techniques, for example, by extraction from a natural source (e.g., cell lines or biological fluids), by expression of a recombinant nucleic acid encoding the polypeptide, or by chemically synthesizing the polypeptide. Purity can be measured by any appropriate method, e.g., by column chromatography, polyacrylamide gel electrophoresis, or high pressure liquid chromatography (HPLC) analysis. Alternatively, a polypeptide is considered isolated if it has been altered by human intervention, placed in a location that is not its natural site, or if it is introduced into one or more cells.

The peptides and polypeptides of the invention, as defined above, include all "mimetic" and "peptidomimetic" forms. The terms "mimetic" and "peptidomimetic" refer to a synthetic chemical compound that has substantially the same structural and/or functional characteristics of the peptides or polypeptides of the invention. The mimetic can be either entirely composed of synthetic, non-natural analogs of amino acids or may be a chimeric molecule of natural amino acids and non-natural analogs of amino acids. The mimetic can also incorporate any amount of conservative substitutions, as long as such substitutions do not substantially alter the mimetic's structure or activity.

By "preventing" or "reducing the likelihood of" is meant reducing the severity, the frequency, and/or the duration of a disease or disorder (e.g., myocardial infarction or peripheral vascular disease) or the symptoms thereof.

By "protease protective organic group" is meant an organic group, other than a proteinogenic amino acid, that, when added to the N-terminal amino acid of SDF-1 or a mutated form of SDF-1 (mSDF-1), results in a modified peptide that maintains at least, for example, 10, 15, 20, 25, 30, 40, 50, 60, 70, 80, 90, 95, 99, or 100% of the chemoattractant activity of unmodified SDF-1 (as determined by, e.g., assays of Jurkat T cell migration or other assays known in the art to measure chemotaxis) and that is inactivated by an enzyme (e.g., DPPIV) at a rate of less than, for example, 50, 45, 40, 35, 30, 25, 20, 15, 10, 5, or 1% of the rate of inactivation of unmodified SDF-1.

By "protease resistant" is meant a peptide or polypeptide that contains one or more modifications in its primary sequence of amino acids compared to a native or wild-type peptide or polypeptide (e.g., native or wild-type SDF-1) and exhibits increased resistance to proteolysis compared to the native or wild-type peptide or polypeptide without the one or more amino acid modifications. By "increased protease resistance" is meant an increase as assessed by in vitro or in vivo assays, as compared to the peptide or polypeptide absent the amino acid sequence changes. Increased resistance to proteases can be assessed by testing for activity or expression following exposure to particular proteases (e.g., MMP-2, MMP-9, DPPIV, leukocyte elastase, cathepsin G, carboxypeptidase M, or carboxypeptidase N) using assays such as, for example, Jurkat T-lymphocyte migration assays, CXCR-4-cAMP receptor activation assays, and CXCR4- or CXCR7-β-arrestin assays. Typically, the increase in protease resistance is at least about 1%, 2%, 3%, 4%, 5%, 6%, 7%, 8%, 9%, 10%, 20%, 30%, 40%, 50%, 60%, 70%, 80%, 90%, 91%, 92%, 93%, 94%, 95%, 96%, 97%, 98%, 99%, 100%, 200%, 300%, 400%, 500%, or more compared to the same peptide or polypeptide, absent the changes in amino acid sequence that confer the resistance.

By "proteinogenic" is meant that the amino acids of a polypeptide or peptide are the L-isomers of: alanine (A); arginine (R); asparagine (N); aspartic acid (D); cysteine (C); glutamic acid (E); glutamine (Q); glycine (G); histidine (H); isoleucine (I); leucine (L); lysine (K); methionine (M); phenylalanine (F); proline (P); serine (S); threonine (T); tryptophan (W); tyrosine (Y); or valine (V).

By "SDF" or "SDF-1" is meant a stromal cell derived factor peptide which can include the sequence of SEQ ID NO:52 or any of the multiple forms of SDF (e.g., SDF-1α (CXCL12a), SDF-1β (CXCL12b), and SDF-γ, produced by alternate splicing of the same gene). SDF-1β includes an additional four amino acid residues at the C-terminus of SDF-1α, Arg-Phe-Lys-Met. The first three exons of SDF-1γ are identical to those of SDF-1α and SDF-1β. The fourth exon of SDF-1γ is located 3200 base-pairs downstream from the third exon on the SDF-1 locus and lies between the third exon and the fourth exon of SDF-1β. Although SEQ ID NO:52 shows the sequence of SDF-1α, this sequence may be extended at the C-terminus to include additional amino acid residues. The invention includes mutations of SDF-1α, SDF-1β, and SDF-γ. For the purposes of the present invention, the term "SDF" or "SDF-1" refers to the active form of the peptide, i.e., after cleavage of the signal peptide.

By "mSDF-1," "mSDF," or "SDF(NqN')" (where N is the one letter designation of the amino acid originally present, q is its position from the N-terminus of the peptide, and N' is the amino acid that has replaced N) is meant a mutant SDF-1 peptide. Peptides that have been mutated by the addition of amino acids (e.g., one or more amino acids) at the N-terminus are abbreviated "$X_p$-R," where X is a proteinogenic amino acid or protease protective organic group, p is an integer, and R is the peptide prior to extension (e.g., SDF-1 or mSDF-1). For example, "S-SDF-1" or "S-mSDF-1" is an SDF-1 or mSDF-1 molecule, respectively, with a serine residue added at the N-terminus. Peptides that have been mutated by the addition of amino acids (e.g., one or more amino acids) at the C-terminus are abbreviated "R-$Y_z$," where Y is a proteinogenic amino acid or protease protective organic group, z is an integer, and R is the peptide prior to extension (e.g., SDF-1, mSDF-1, or $X_p$-mSDF-1). Unless otherwise indicated, all pharmaceutically acceptable forms of peptides may be used, including all pharmaceutically acceptable salts.

By "SDF-1 or mutant SDF-1 peptide of the invention" is meant any wild-type SDF-1 (including isoforms) or mutant SDF-1 peptides described herein. Also included in the term are compositions (e.g., pharmaceutical compositions) that include the wild-type SDF-1 or mutant SDF-1 peptides described herein.

By "subject" is meant a mammal, including, but not limited to, a human or non-human mammal, such as a bovine, equine, canine, ovine, or feline.

By "sustained release" or "controlled release" is meant that the therapeutically active component is released from the formulation at a controlled rate such that therapeutically beneficial levels (but below toxic levels) of the component are maintained over an extended period of time ranging from, e.g., about 12 hours to about 4 weeks (e.g., 12 hours, 24 hours, 48 hours, 1 week, 2 weeks, 3 weeks, or 4 weeks), thus providing, for example, a 12-hour to a 4-week dosage form.

By "treating" or "ameliorating" is meant administering a pharmaceutical composition for therapeutic purposes or administering treatment to a subject already suffering from a disorder to improve the subject's condition. By "treating a disorder" or "ameliorating a disorder" is meant that the disorder and the symptoms associated with the disorder are, e.g., alleviated, reduced, cured, or placed in a state of remission. As compared with an equivalent untreated control, such amelioration or degree of treatment is at least 5%, 10%, 20%, 30%, 40%, 50%, 60%, 70%, 80%, 90%, 95%, 99%, or 100%, as measured by any standard technique.

Other features and advantages of the invention will be apparent from the detailed description and from the claims.

BRIEF DESCRIPTION OF THE DRAWINGS

FIG. 1 is a bar graph showing that SSDF-1(S4V) delivered IV and 7 days post ischemia reperfusion injury improves Ejection Fraction by 10 percentage points compared to the PBS control.

DETAILED DESCRIPTION

The present invention is based upon the discovery that the recovery of damaged tissue, e.g., damaged cardiac tissue, is promoted by intravenous administration of wild-type SDF-1 or SDF-1 that has been mutated to increase resistance to enzymatic cleavage (e.g., cleavage by one or more of MMP-2, MMP-9, DPPIV, leukocyte elastase, cathepsin G, carboxypeptidase M, or carboxypeptidase N). Such peptides may be administered as isolated peptides, with or without a pharmaceutically acceptable carrier. In addition, we have surprisingly discovered that delayed administration from within minutes after initial occurrence of the tissue damage or after onset, recognition, or diagnosis of the disease or condition, to within 1 hour, 2 hours, 3 hours, 4 hours, 6 hours, 12 hours, 24 hours, at least 48 hours, at least 3 days, 4 days, 5 days, 6 days, 7 days, 10 days, 2 weeks, one month, two months, three months, six months, one year, two years, or more after initial occurrence of the tissue damage or after onset, recognition, or diagnosis of the disease or condition is also useful in promoting the recovery of damaged tissue.

Intravenous Administration

SDF-1 or mutant. SDF-1 peptide-containing compositions used in the methods of the present invention are administered intravenously, for example, by intravenous (IV) injection or using an implantable device (e.g., a catheter). Intravenous administration generally involves injections into any accessible vein in the body of a mammal, including but not limited to a peripheral vein (e.g., a vein on the arm, a vein in the leg, the back of the hand, or the median cubital vein) or via a central line to a large vein (e.g., the superior vena cava or inferior vena cava or within the right atrium of the heart). Intravenous administration can also include administration by peripherally inserted central catheter, central venous lines, or implantable ports.

A peripheral IV line consists of a short catheter (a few centimeters long) inserted through the skin into a peripheral vein (e.g., any vein that is not inside the chest or abdomen) using, for example, a cannula-over-needle device, in which a flexible plastic cannula comes mounted on a metal trocar. The part of the catheter that remains outside the skin is called the connecting hub; it can be connected to a syringe or an intravenous infusion line. Ported cannulae have an injection port on the top that may be used to administer the SDF-1 mutant SDF-1 peptides of the invention.

Peripherally inserted central catheter (PICC) lines are used when IV access is required over a prolonged period of time or when the material to be infused would cause quick damage and early failure of a peripheral IV and when a conventional central line may be too dangerous to attempt.

Also included in IV delivery methods of the invention are central venous lines in which, for example, a catheter is inserted into a subclavian internal jugular or a femoral vein and advanced toward the heart until it reaches the superior vena cava or right atrium.

Another central IV delivery method is through the use of a central IV line which flows through a catheter with its tip within a large vein, usually the superior vena cava or inferior vena cava or within the right atrium of the heart.

Another type of central line useful in the IV delivery methods of the invention is a Hickman line or Broviac catheter, which is inserted into the target vein and then "tunneled" under the skin to emerge a short distance away.

Implantable ports are also used for IV delivery of the SDF-1 and mutant SDF-1 peptide compounds of the invention. An implantable port is a central venous line that does not have an external connector; instead, it has a small reservoir that is covered with silicone rubber and is implanted under the skin. The peptide compounds are administered intermittently by placing a small needle through the skin, piercing the silicone, into the reservoir. A port can be left in a subject's body for weeks, months, even years. Intermittent infusion is another type of intravenous administration that can be used when a subject requires administration of the SDF-1 and mSDF-1 peptide compounds of the invention only at certain times.

An SDF-1 or mSDF-1 peptide-containing composition may be administered into one vein or several veins. The SDF-1 or mSDF-1 peptide-containing composition can be intravenously administered for a period of about 1 minute, 1 to 5 minutes, 10 to 20 minutes, 20 to 30 minutes, or for a sufficient time as determined by the clinician into, for example, one or more veins. The administration can be repeated intermittently to achieve or sustain the predicted benefit. The timing for repeat administration is based on the subject's response, for example, by monitoring symptoms associated with tissue damage. A therapeutically effective dose or amount of an SDF-1 or mSDF-1 peptide-containing composition that is to be given can be divided into two or more doses, and a dose may be administered into two or more veins with a single puncture or multiple punctures.

SDF-1 and Protease-Resistant Mutants

SDF-1 is a small cytokine belonging to the chemokine family that is officially designated chemokine (C-X-C motif) ligand 12 (CXCL12). SDF-1 is produced in multiple forms, SDF-1α (CXCL12a), SDF-1β (CXCL12b), and SDF-1γ, by alternate splicing of the same gene.

Unmutated SDF-1α has the following sequence:

```
                                        (SEQ ID NO: 52)
K P V S L S Y R C P C R F F E S H V A R A N V K H L K I L N T P N C A L Q I V A R L K

N N N R Q V C I D P K L K W I Q E Y L E K A L N K
```

The SDF-1 peptides described herein include SDF-1 peptides with mutations to render the peptides resistant to, for example, matrix metalloproteinase-2 (MMP-2), matrix metalloproteinase-9 (MMP-9), dipeptidyl peptidase IV (DP-PIV), leukocyte elastase, cathepsin G, carboxypeptidase M, or carboxypeptidase N. In the methods of the present invention, unmutated SDF-1 may also be administered by intravenous delivery for treatment or amelioration of tissue damage.

The methods of the invention feature mutant forms of SDF-1 (mSDF-1), which are characterized by a change in the third, fourth, fifth, and/or sixth amino acid residue from the N-terminus of unmutated SDF-1. mSDF-1 peptides of the invention have at least amino acids 1-8 of SEQ ID NO:53 and may be extended at the C-terminus by all or any portion of the remaining sequence of SEQ ID NO:53, which has the following sequence:

(SEQ ID NO: 53)

K P $X_3$ $X_4$ $X_5$ $X_6$ Y R C P C R F F E S H V A R A N V K H L K I L N T P N C A L Q I V A R L

K N N N R Q V C I D P K L K W I Q E Y L E K A L N K, wherein $X_3$, $X_4$, $X_5$, and $X_6$ are any amino acid residue.

In certain embodiments, $X_3$ is valine, histidine, or cysteine.

In certain embodiments, $X_4$ is serine or valine.

In certain embodiments, $X_5$ is leucine, proline, threonine, or valine.

In certain embodiments, $X_6$ is serine, cysteine, or glycine.

For example, the mSDF-1 peptide may include a mutation at the fourth (e.g., Ser→Val) and/or fifth (e.g., Leu→Pro) amino acid position.

(SEQ ID NO: 63)

K P V <u>V</u> L S Y R C P C R F F E S H V A R A N V K H L K I L N T P N C A L Q I V A R L K

N N N R Q V C I D P K L K W I Q E Y L E K A L N K (SEQ ID NO: 64)

K P V S <u>P</u> S Y R C P C R F F E S H V A R A N V K H L K I L N T P N C A L Q I V A R L K

N N N R Q V C I D P K L K W I Q E Y L E K A L N K (SEQ ID NO: 65)

K P V <u>V</u> <u>P</u> S Y R C P C R F F E S H V A R A N V K H L K I L N T P N C A L Q I V A R L K

N N N R Q V C I D P K L K W I Q E Y L E K A L N K

In another example, the mSDF-1 peptide may include a Val→His (SEQ ID NO:54) or Val→Cys (SEQ ID NO:55) mutation at the third amino acid position.

(SEQ ID NO: 54)

K P <u>H</u> S L S Y R C P C R F F E S H V A R A N V K H L K I L N T P N C A L Q I V A R L K

N N N R Q V C I D P K L K W I Q E Y L E K A L N K (SEQ ID NO: 55)

K P <u>C</u> S L S Y R C P C R F F E S H V A R A N V K H L K I L N T P N C A L Q I V A R L K

N N N R Q V C I D P K L K W I Q E Y L E K A L N K

In other embodiments, the mSDF-1 peptide may include a Leu→Thr (SEQ ID NO:56) or Leu→Val (SEQ ID NO:60) mutation at the fifth amino acid position.

(SEQ ID NO: 56)

K P V S <u>T</u> S Y R C P C R F F E S H V A R A N V K H L K I L N T P N C A L Q I V A R L K

N N N R Q V C I D P K L K W I Q E Y L E K A L N K

-continued (SEQ ID NO: 60)

K P V S V S Y R C P C R F F E S H V A R A N V K H L K I L N T P N C A L Q I V A R L K

N N N R Q V C I D P K L K W I Q E Y L E K A L N K

In other embodiments, the mSDF-1 peptide may include a Ser→Cys (SEQ ID NO:61) or Ser→Gly (SEQ ID NO:62) mutation at the sixth amino acid position.

(SEQ ID NO: 61)

K P V S L C Y R C P C R F F E S H V A R A N V K H L K I L N T P N C A L Q I V A R L K

N N N R Q V C I D P K L K W I Q E Y L E K A L N K (SEQ ID NO: 62)

K P V S L G Y R C P C R F F E S H V A R A N V K H L K I L N T P N C A L Q I V A R L K

N N N R Q V C I D P K L K W I Q E Y L E K A L N K

The methods of the invention may also include peptides that encompass any combination of the mutations described herein. For example, the mSDF-1 peptides may include a Val→Cys mutation at the third amino acid position of SEQ ID NO:53 and a Ser→Cys mutation at the sixth amino acid position of SEQ ID NO:53.

Mutations made to the SDF-1 peptides to confer protease resistance may also include, for example, the addition of a moiety (e.g., a proteinogenic amino acid or protease protective organic group) to the N-terminus of, e.g., the mSDF-1 peptides (described above), yielding $X_p$-mSDF-1. For example, X may be: $R^1$—$(CH_2)_d$—, where d is an integer from 0-3, and $R^1$ is selected from: hydrogen (with the caveat that when $R^1$ is hydrogen, d must be at least 1); a branched or straight $C_1$-$C_3$ alkyl; a straight or branched $C_2$-$C_3$ alkenyl; a halogen, $CF_3$; —$CONR^5R^4$; —$COOR^5$; —$COR^5$; —$(CH_2)_qNR^5R^4$; —$(CH_2)_qSOR^5$; —$(CH_2)_qSO_2R^5$, —$(CH_2)_qSO_2NR^5R^4$; and $OR^5$, where $R^4$ and $R^5$ are each independently hydrogen or a straight or branched $C_1$-$C_3$ alkyl. In instances where an organic group is used for X, p should be 1. X may also represent a proteinogenic amino acid, wherein, for example, 1-10 (e.g., 1-9, 1-8, 1-7, 1-6, 1-5, 1-4, 1-3, 1-2, or 1) amino acid(s) is/are added to the N-terminus of SDF-1 (e.g., mSDF-1), and one or more of these added amino acids may he substituted with a protease protective organic group. For example, a proteinogenic amino acid (e.g., serine) or protease protective organic group may be added to the N-terminus of SDF-1 (e.g., mSDF-1) to confer, for example, resistance to DPPIV cleavage without substantially changing the chemoattractant activity or resistance to other proteases (e.g., MMP-2). The sequences below represent exemplary SDF-1 mutants with a serine amino acid added to the N-terminus.

(SEQ ID NO: 68)

S K P $X_3$ $X_4$ $X_5$ $X_6$ Y R C P C R F F E S H V A R A N V K H L K I L N T P N C A L Q I V A R

L K N N N R Q V C I D P K L K W I Q E Y L E K A L N K, wherein $X_3$, $X_4$, $X_5$, and $X_6$ are any amino acid residue.

In certain embodiments, $X_3$ is valine, histidine, or cysteine.

In certain embodiments, $X_4$ is serine or valine.

In certain embodiments, $X_5$ is leucine, proline, threonine, or valine.

In certain embodiments, $X_6$ is serine, cysteine, or glycine.

Specific examples of sequences include:

(SEQ ID NO: 69)

S K P V V L S Y R C P C R F F E S H V A R A N V K H L K I L N T P N C A L Q I V A R L

K N N N R Q V C I D P K L K W I Q E Y L E K A L N K (SEQ ID NO: 70)

S K P V S P S Y R C P C R F F E S H V A R A N V K H L K I L N T P N C A L Q I V A R L K

N N N R Q V C I D P K L K W I Q E Y L E K A L N K (SEQ ID NO: 71)

S K P V V P S Y R C P C R F F E S H V A R A N V K H L K I L N T P N C A L Q I V A R L

K N N N R Q V C I D P K L K W I Q E Y L E K A L N K (SEQ ID NO: 72)

S K P H S L S Y R C P C R F F E S H V A R A N V K H L K I L N T P N C A L Q I V A R L

K N N N R Q V C I D P K L K W I Q E Y L E K A L N K

-continued (SEQ ID NO: 73)
S K P C S L S Y R C P C R F F E S H V A R A N V K H L K I L N T P N C A L Q I V A R L K

N N N R Q V C I D P K L K W I Q E Y L E K A L N K (SEQ ID NO: 74)
S K P V S T S Y R C P C R F F E S H V A R A N V K H L K I L N T P N C A L Q I V A R L

K N N N R Q V C I D P K L K W I Q E Y L E K A L N K (SEQ ID NO: 75)
S K P V S V S Y R C P C R F F E S H V A R A N V K H L K I L N T P N C A L Q I V A R L

K N N N R Q V C I D P K L K W I Q E Y L E K A L N K (SEQ ID NO: 76)
S K P V S L C Y R C P C R F F E S H V A R A N V K H L K I L N T P N C A L Q I V A R L

K N N N R Q V C I D P K L K W I Q E Y L E K A L N K (SEQ ID NO: 77)
S K P V S L G Y R C P C R F F E S H V A R A N V K H L K I L N T P N C A L Q I V A R L

K N N N R Q V C I D P K L K W I Q E Y L E K A L N K

Mutations made to the SDF-1 peptides to confer protease resistance may also include, for example, the addition of a moiety (e.g., a proteinogenic amino acid) to the C-terminus of, e.g., the mSDF-1 peptides (described above), yielding mSDF-1-$Y_z$ or $X_p$-mSDF-1-$Y_z$. Y may represent a proteinogenic amino acid, wherein, for example, 1-10 (e.g., 1-9, 1-8, 1-7, 1-6, 1-5, 1-4, 1-3, 1-2, or 1) amino acid(s) is/are added to the C-terminus of SDF-1 (e.g., mSDF-1 or $X_p$-mSDF-1). For example, a proteinogenic amino acid (e.g., serine) may be added to the C-terminus of SDF-1, mSDF-1, or $X_p$-mSDF-1 to confer, for example, resistance to carboxypeptidase M or carboxypeptidase N cleavage without substantially changing the chemoattractant activity or resistance to other proteases (e.g., MMP-2). In one embodiment, the invention features an isolated mSDF-1-$Y_z$ or $X_p$-mSDF-1-$Y_z$ peptide, wherein SDF-1 includes the amino acid sequence of SEQ ID NO:53. However, C-terminal modifications may be made to SDF-1 and any of the SDF-1 peptides described herein. The mutated SDF-1 peptides described herein retain their ability to act as chemoattractants, but are resistant to enzymatic (e.g., proteolytic) digestion. The mSDF-1 peptides maintain chemoattractant activity with a sensitivity (as determined by, e.g., the effective concentration needed to obtain 50% of maximal response in the assays of, e.g., Jurkat T cell migration or any other chemotaxis assay known in the art) of at least, for example, 10, 15, 20, 25, 30, 40, 50, 60, 70, 80, 90, 95, 99, or 100% of the sensitivity of unmutated SDF-1. Loss of chemoattractant activity may be due to cleavage by, for example, MMP-2, MMP-9, leukocyte elastase, DPPIV, cathepsin G, carboxypeptidase M, or carboxypeptidase N. The rate of inactivation of mSDF-1 may be less than, for example, 50, 45, 40, 35, 30, 25, 20, 15, 10, 5, or 1% of the rate of inactivation of SDF-1.

The mutated SDF-1 peptides may be resistant to cleavage by, for example, MMP-2, MMP-9, DPPIV, leukocyte elastase, cathepsin G, carboxypeptidase M, or carboxypeptidase N. Thus, they are ideally suited for use at sites such as, e.g., damaged tissue (e.g., damaged cardiac tissue), where proteolytic enzymes are present at high concentrations, or delivery to the site via the blood or plasma. Accordingly, mutated SDF-1 peptides are suitable for intravenous administration due to the improved stability of such peptides.

Protease-resistant SDF-1 peptides described herein may include amino acids or sequences modified either by natural processes, such as posttranslational processing, or by chemical modification using techniques known in the art. Modifications may occur anywhere in a polypeptide, including the polypeptide backbone, the amino acid side-chains, and the amino- or carboxy-terminus. The same type of modification may be present in the same or varying degrees at several sites in a given polypeptide, and a polypeptide may contain more than one type of modification. Modifications include, e.g., PEGylation, acetylation, acylation, addition of acetomidomethyl (Acm) group, ADP-ribosylation, alkylation, amidation, biotinylation, carbamoylation, carboxyethylation, esterification, covalent attachment to fiavin, covalent attachment to a heme moiety, covalent attachment of a nucleotide or nucleotide derivative, covalent attachment of drug, covalent attachment of a marker (e.g., a fluorescent or radioactive marker), covalent attachment of a lipid or lipid derivative, covalent attachment of phosphatidylinositol, cross-linking, cyclization, disulfide bond formation, demethylation, formation of covalent crosslinks, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins (e.g., arginylation), and ubiquitination. Posttranslational modifications also include the addition of polymers to stabilize the peptide or to improve pharmacokinetics or pharmacodynamics. Exemplary polymers include, e.g., poly(2-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), polyglutamic acid (PGA), and polyorthoesters.

Fusion Proteins

The methods of the invention may also utilize fusion proteins in which any of the SDF-1, mSDF-1, $X_p$-mSDF-1, mSDF-1-$Y_z$, or $X_p$-mSDF-1-$Y_z$ peptide sequences described herein are linked to the Fc region of IgG (e.g., human IgG1). Alternatively, the Fc region may be derived from IgA, IgM, IgE, or IgD of humans or other animals, including swine, mice, rabbits, hamsters, goats, rats, and guinea pigs. The Fc region of IgG includes the CH2 and CH3 domains of the IgG heavy chain and the hinge region. The hinge serves as a flexible spacer between the two parts of the Fc fusion protein, allowing each part of the molecule to function independently. The Fc region used in the present invention can be prepared in, for example, monomeric and dimeric form.

An exemplary Fc fusion peptide is S-SDF-1(S4V)-Fc with the following amino acid sequence. The GGGGS linker (SEQ ID NO:66) is indicated in bold and the Fc peptide is underlined.

(SEQ ID NO: 67)

S K P V V L S Y R C P C R F F E S H V A R A N V K H L K I L N T P N C A L Q I V A R L

K N N N R Q V C I D P K L K W I Q E Y L E K A L N K G G G G S V D K T H T C P P C P

A P E L L G G P S V F L F P P K P K D T L Met I S R T P E V T C V V V D V S H E D P E V

K F N W Y V D G V E V H N A K T K P R E E Q Y N S T Y R V V S V L T V L H Q D W L

N G K E Y K C K V S N K A L P A P I E K T I S K A K G Q P R E P Q V Y T L P P S R D E L

T K N Q V S L T C L V K G F Y P S D I A V E W E S N G Q P E N N Y K T T P P V L D S D

G S F F L Y S K L T V D K S R W Q Q G N V F S C S V Met H E A L H N H Y T Q K S L S L

S P G K

Other non-limiting examples of Fc fusion peptides include, e.g., SDF-1(S4V)-Fc, SDF-1(L5P)-Fc, SDF-1(S6C)-Fc, SDF-1(V3H)-Fc, SDF-1-Fc, S-SDF-1-Fc, and SDF-1-Fc.

All of the above proteins are included in the terms "SDF-1 and mSDF-1 proteins of the invention" or "peptides of the invention."

Peptide Synthesis

The SDF-1 or protease-resistant mutant SDF-1 peptides used in the methods of the present invention can be made by solid-phase peptide synthesis using, for example, standard N-tert-butyoxycarbonyl (t-Boc) chemistry and cycles using n-methylpyrolidone chemistry. Exemplary methods for synthesizing peptides are found, for example, in U.S. Pat. Nos. 4,192,798; 4,507,230; 4,749,742; 4,879,371; 4,965,343; 5,175,254; 5,373,053; 5,763,284; and 5,849,954, hereby incorporated by reference. These peptides may also be made using recombinant DNA techniques.

Once peptides have been synthesized, they can be purified using procedures such as, for example, HPLC on reverse-phase columns. Purity may also be assessed by HPLC, and the presence of a correct composition can be determined by amino acid analysis. A purification procedure suitable for mSDF-1 peptides is described, for example, in U.S. Patent Application Publication No. 2008/0095758, hereby incorporated by reference.

Fusion proteins may either be chemically synthesized or made using recombinant DNA techniques. Other non-limiting examples of Fc fusion peptides include, e.g., SDF-1(S4V)-Fc, SDF-1(L5P)-Fc, SDF-1(S6C)-Fc, SDF-1(V3H)-Fc, SDF-1-Fc, S-SDF-1-Fc, and SDF-1-Fc.

Pharmaceutical Compositions and Dosages

Any of the peptides employed in the methods of the present invention may be contained in any appropriate amount in any suitable carrier substance, and the protease-resistant peptides or fusion proteins are generally present in an amount of 1-95% by weight of the total weight of the composition, e.g., 5%, 10%, 20%, or 50%. The protease-resistant SDF-1 peptides or fusion proteins described herein may be incorporated into a pharmaceutical composition containing a carrier such as, e.g., saline, water, Ringer's solution, and other agents or excipients. The composition is designed for intravenous delivery (e.g., by injection or implantable port). Thus, the composition may be in the form of, e.g., suspensions, emulsions, solutions, or injectables. All compositions may be prepared using methods that are standard in the art (see, e.g., *Remington's Pharmaceutical Sciences,* 16th ed., A. Oslo. ed., Easton, Pa. (1980)).

The peptides of the invention can be delivered in a controlled-release or sustained-release system. For example, polymeric materials can be used to achieve controlled or sustained release of the peptides (see, e.g., Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, N.Y. (1984); U.S. Pat. Nos. 5,679,377; 5,916,597; 5,912,015; 5,989,463; and 5,128,326; PCT Publication Nos. WO 99/15154 and WO 99/20253, hereby incorporated by reference). Examples of polymers used in sustained-release formulations include, e.g., poly(2-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), polyglutamic acid (PGA), and polyorthoesters.

It is expected that the skilled practitioner can adjust dosages of the peptide on a case by case basis using methods well established in clinical medicine. The optimal dosage may be determined by methods known in the art and may be influenced by factors such as the age of the subject being treated, disease state, and other clinically relevant factors. Generally, when administered to a human, the dosage of any of the therapeutic agents (e.g., SDF-1 or protease-resistant mutant SDF-1 peptides) described herein will depend on the nature of the agent and can readily be determined by one skilled in the art. Typically, such a dosage is normally about 0.001 μg to 2000 mg per day, desirably about 1 mg to 1000 mg per day, and more desirably about 5 mg to 500 mg per day. In one embodiment the dosage is 0.01 mg/kg to 100 mg/kg, or desirably 1 mg/kg to 10 mg/kg per day.

The peptides of the invention may be administered intravenously once, twice, three times, four times, or five times each day; once per week, twice per week, three times per week, four times per week, five times per week, or six times per week; once per month, once every two months, once every three months, or once every six months; or once per year. Alternatively, the peptides of the invention may be administered one or two times and repeated administration may not be needed. Administration of the peptides described herein can continue until tissue damage (e.g., tissue damage resulting from myocardial infarction or peripheral vascular disease) has healed or has been ameliorated. The duration of therapy can be, e.g., one day to one week, one week to one month, one week to one year, or one week to more than one year; alternatively, the peptides of the invention can be administered for a shorter or a longer duration. Continuous daily dosing with the peptides may not be required. A therapeutic regimen may require cycles, during which time a composition is not administered, or therapy may be provided on an as-needed basis.

The SDF-1 or mutant SDF-1 peptides of the invention may be delivered immediately at the time of tissue damage or within minutes after initial occurrence of the tissue damage or after onset, recognition, or diagnosis of the disease or condition (e.g., post myocardial infarction). The SDF-1 or mutant SDF-1 peptides of the invention can also be delivered after a short or long delay following the initial tissue damage. For example, the SDF-1 or mutant SDF-1 peptides of the invention can be delivered at any period after the initial damage occurs ranging from several minutes to within 1 hour, 2 hours, 3 hours, 4 hours, 6 hours, 12 hours, 24 hours, at least 48 hours, at least 3 days, 4 days, 5 days, 6 days, 7 days, 10 days, 2 weeks, one month, two months, three months, six months, one year, two years, or more after initial occurrence of the tissue damage or after onset, recognition, or diagnosis of the disease or condition. For tissue damage that is more chronic in nature and occurs over time, including but not limited to PVD or diabetic wounds, the SDF-1 or mutant SDF-1 peptides of the invention may be delivered immediately after the onset of the damage or immediately after the diagnosis or initial or subsequent indications of the damage (e.g., PVD or diabetic wounds). In such cases, the delivery of the SDF-1 or mutant SDF-1 peptides of the invention may be three days, seven days, one week, two weeks, three weeks, a month, two months, three months, four months, five months, six months, or even a year or more after the tissue damage has occurred or after onset, recognition, or diagnosis of the tissue damage or disease or condition.

For any type of tissue damage, disease, or disorder described herein, initial IV administration of the SDF-1 or mutant SDF-1 peptides of the invention may be at a time ranging from minutes to two years after the initial occurrence, recognition or diagnosis of tissue damage, or one hour to two years after the initial occurrence, recognition or diagnosis of tissue damage, one day to one year after the initial occurrence, recognition or diagnosis of tissue damage, one day to six months after the initial occurrence, recognition or diagnosis of tissue damage, one month to six months after the initial occurrence, recognition or diagnosis of tissue damage, one day to one month after the initial occurrence, recognition or diagnosis of tissue damage, one week to one month after the initial occurrence, recognition or diagnosis of tissue damage, one week to two weeks after the initial occurrence, recognition or diagnosis of tissue damage, one hour to one week after the initial occurrence, recognition or diagnosis of tissue damage, one hour to three days after the initial occurrence, recognition or diagnosis of tissue damage, or several minutes to one hour after the initial occurrence, recognition or diagnosis of tissue damage.

The SDF-1 or mutant SDF-1 peptides of the invention may be delivered once over the duration of therapy or multiple times over the duration of therapy. Depending on the severity of the tissue damage, the SDF-1 or mutant SDF-1 peptides of the invention may be delivered repeatedly over time to ensure repair or recovery of the damaged tissue.

In addition, the intravenous delivery of the SDF-1 or mutant SDF-1 peptides of the invention may be combined with additional forms of delivery of the SDF-1 or mutant SDF-1 peptides of the invention. In one example, after a myocardial infarction, SDF-1 or mutant SDF-1 peptides of the invention may be delivered initially via intra-coronary or intra-arterial methods and then followed by subsequent delivery via intravenous methods starting 1 day, 2 days, 3 days, 4 days, 5 days, 6 days, 7 days, 2 weeks, 1 month, 2 month, 3 months, 4 months, 5 months, 6 months, one year, or more after the initial delivery. Here again, depending on the severity of the tissue damage, the SDF-1 or mutant SDF-1 peptides of the invention may be delivered repeatedly over time to ensure repair or recovery of the damaged tissue.

Appropriate dosages of the peptides used in the methods of the invention depend on several factors, including the administration method, the severity of the disorder, and the age, weight, and health of the subject to be treated. Additionally, pharmacogenomic information (e.g., the effect of genotype on the pharmacokinetic, pharmacodynamic, or efficacy profile of a therapeutic) about a particular subject may affect the dosage used.

Diagnosis and Treatment

The methods of the present invention are useful for treating any subject that has been diagnosed with or has suffered from tissue damage (e.g., damage to cardiac tissue due to myocardial infarction or tissue damage resulting from peripheral vascular disease) or wounds (e.g., diabetic wounds). Tissue damage may be the result of, for example, a cardiovascular condition (e.g., myocardial infarction); peripheral vascular disease (PVD); peripheral artery disease (PAD); ulcers (e.g.,skin wound ulcers); surgery; or diabetes. The methods of the present invention may be used to promote wound healing or tissue repair. One skilled in the art will understand that subjects of the invention may have been subjected to standard tests or may have been identified, without examination, as one at high risk due to the presence of one or more risk factors. Diagnosis of these disorders may be performed using any standard method known in the art.

The methods described herein may also be used to treat any disease or condition characterized by a high concentration of protease (e.g., MMP-2, MMP-9, DPPIV, leukocyte elastase, cathepsin G, carboxypeptidase M, and/or carboxypeptidase N), where the attraction of stem cells upon the administration of a protease-resistant SDF-1 peptide may induce regeneration or healing. Exemplary disorders to be treated by compositions of the present invention include inflammatory and ischemic diseases (e.g., myocardial infarction, stroke or limb ischemia), wound healing, and diabetic ulcers.

The efficacy of treatment can be monitored using methods known to one of skill in the art including, e.g., assessing symptoms of the disease or disorder, physical examination, histopathological examination, blood chemistry analysis, computed tomography, cytological examination, and magnetic resonance imaging. In certain embodiments, hemodynamic data is collected to determine the efficacy of treatment. Hemodynamic tests may include, e.g., determining an ejection fraction (e.g., fraction of blood pumped out of ventricles with each heart beat), determining end diastolic pressure, and determining end systolic elastance (e.g., volume of blood present in the left ventricle). In one example, hemodynamic tests may be used to monitor cardiac function in a subject that has suffered tissue damage resulting from myocardial infarction or other form of cardiac ischemia.

The methods of the present invention may be used in combination with additional therapies to promote wound healing or tissue repair. Treatment therapies that can be used in combination with the methods of the invention include, but are not limited to, heparin, β-blockers (e.g., atenolol, metoprolol, nadolol, oxprenolol, pindolol, propranolol, or timolol), angiotensin-converting enzyme (ACE) inhibitors (e.g., captopril, enalapril, fosinopril, lisinopril, perindopril, quinapril, ramipril, trandolapril, or benazepril), angiotensin II receptor blockers (e.g., candesartan, eprosartan, irbesartan, losartan, olmesartan, telmisartan, or valsartan), diuretics, aspirin, cholesterol-lowering drugs (e.g., HMG-CoA reductase inhibitors (e.g., atorvastatin, cerivastatin, fluvastatin, lovastatin, mevastatin, pitavastatin, pravastatin, rosuvastatin, or simvastatin)), cell therapy, anti-platelet drugs (e.g., clopidogrel, prasugrel, ticlopidine, cilostazol, abciximab, eptifibatide, tirofiban, or dipyridamole), anti-hypertensive drugs, anti-arrhythmic drugs (e.g., quinidine, procainamide, disopyramide, lidocaine, mexiletine, tocainide, phenytoin, moricizine, flecainide, sotalol, ibutilide, amiodarone, bretylium, dofetilide, diltiazem, or verapamil), angiogenic drugs, wound dressings, PDGF, and/or negative pressure devices and therapies.

EXAMPLES

The present invention is illustrated by the following example, which is in no way intended to be limiting of the invention.

Example 1

Delayed and IV Dosing of Protease Resistant SDF-1 Variants Improve Cardiac Function in a Rodent Ischemia Reperfusion Model In the following example, we describe experiments demonstrating that intravenous delivery and long term delayed dosing of an mSDF-1 peptide-containing composition improves cardiac function in an ischemia reperfusion model.

Rats were anesthetized with 0.05 mg/kg of buprenorphine and 2-3% of isoflurane. After intubation, the chest was opened between ribs 4 and 5, and the left anterior descending (LAD) coronary artery was ligated for 90 minutes. After 90 minutes, the suture was removed from the LAD to initiate reperfusion in the infarct zone. The chest and skin of the rats were then closed. mSDF-1 peptide was administered by intravenous injection 7 days post infarction (>15 rats per group). For intravenous injection, 100 μl of S-SDF-1 (S4V) (at doses of 0, 0.1, and 1.0 mg/kg) in PBS were injected into the tail veins of rats.

In each of the experiments described above, hemodynamic function in the rats was analyzed in a randomized and blinded study four weeks after intravenous dosing (five weeks post the ischemia reperfusion injury). Rats were anesthetized with 0.05 mg/kg of buprenorphine and 2-3% of isoflurane. A 16G endotracheal tube was inserted into the rats and mechanical ventilation was started. The left jugular vein was cannulated with PE 10 to deliver hyperosmotic saline (50 μl of a 25% NaCl solution in water). Hyperosmotic saline was used to measure parallel conductance of the volume measurements.

To determine the ejection fraction and intra-ventricular pressure, the right carotid artery was cannulated. A pressure-volume catheter was inserted and passed into the left ventricle. A baseline pressure-volume measurement was obtained. A hyperosmotic saline solution (described above) was injected into the jugular vein, and a pressure-volume measurement was then obtained.

Our results showed that intravenous injection of S-SDF-1(S4V) delivered 7 days post ischemia reperfusion injury resulted in a 10% improvement in the measured ejection fraction in rats compared to the PBS control (FIG. 1).

OTHER EMBODIMENTS

From the foregoing description, it is apparent that variations and modifications may be made to the invention described herein to adopt it to various usages and conditions. Such embodiments are also within the scope of the following claims.

All publications, patent applications, and patents, mentioned in this specification are herein incorporated by reference to the same extent as if each independent publication or patent application was specifically and individually indicated to be incorporated by reference.

What is claimed is:

1. A method of treating or ameliorating tissue damage in a subject in need thereof, said tissue damage resulting from a disease or condition selected from the group consisting of stroke, myocardial infarction, chronic heart failure, and diabetic wound healing, wherein said method comprises intravenously administering a composition comprising an isolated mutant form of stromal cell derived factor-1 (SDF-1) peptide comprising the formula of a mutant SDF-1 (mSDF-1), mSDF-1-$Y_z$, $X_p$-mSDF-1, or $X_p$-mSDF-1-$Y_z$, wherein said mSDF-1 is a peptide comprising the amino acid sequence of at least amino acids 1-8 of SEQ ID NO:53 and which is optionally extended at the C-terminus by all or any portion of the remaining sequence of SEQ ID NO:53, said SEQ ID NO:53 comprising the amino acid sequence:

(SEQ ID NO: 53)

K P $X_3$ $X_4$ $X_5$ $X_6$ Y R C P C R F F E S H V A R A N V K H

L K I L N T P N C A L Q I V A R L K N N N R Q V C I

D P K L K W I Q E Y L E K A L N K, wherein $X_3$, $X_4$, $X_5$, and $X_6$ are any amino acid, and wherein $X_p$ is a proteinogenic amino acid(s) or a protease protective organic group and p is any integer from 1 to 4;

$Y_z$ is a proteinogenic amino acid(s) or protease protective organic group and z is any integer from 1 to 4;

said mSDF-1 or said mSDF-1-$Y_z$ maintains chemoattractant activity for T cells and is inactivated by matrix metalloproteinase-2 (MMP-2), matrix metalloproteinase-9 (MMP-9), leukocyte elastase, and/or cathepsin G at a rate that is at least50% less than the rate of inactivation of native SDF-1; and said $X_p$-mSDF-1 or said $X_p$-mSDF-1-$Y_z$ maintains chemoattractant activity for T cells, is inactivated by dipeptidyl peptidase IV (DPPIV) at a rate that is at least 50% less than the rate at which native SDF-1 is inactivated, and is inactivated by MMP-2, MMP-9, leukocyte elastase, and/or cathepsin G at a rate that is at least 50% less than the rate of inactivation of native SDF-1;

wherein said isolated mutant form of SDF-1 peptide does not comprise the amino acid sequence of at least amino acids 1-8 of SEQ ID NO:52 and is administered intravenously in an amount sufficient to treat or ameliorate said tissue damage in said subject;

and wherein said composition is initially administered:

a) 24 hours or more after onset or diagnosis of said disease, condition, or tissue damage;

b) 48 hours or more after onset or diagnosis of said disease, condition, or tissue damage;

c) 7 days or more after onset or diagnosis of said disease, condition, or tissue damage;

d) one month or more after onset or diagnosis of said disease, condition, or tissue damage; or e) six months or more after onset or diagnosis of said disease, condition, or tissue damage.

2. The method of claim 1, wherein said $X_3$ is valine, histidine, or cysteine.

3. The method of claim 1, wherein said $X_4$ is serine or valine.

4. The method of claim 1, wherein said $X_5$ is leucine, proline, threonine, or valine.

5. The method of claim 1, wherein said $X_6$ is serine, cysteine, or glycine.

6. The method of claim 1, wherein said peptide is an $X_p$-mSDF-1 peptide or $X_p$-mSDF-1-$Y_z$ peptide and wherein X is a serine and p is 1.

7. The method of claim 1, wherein said peptide is an mSDF-1-$Y_z$ peptide or $X_p$-mSDF-1-$Y_z$ peptide and wherein Y is a serine and z is 1.

8. The method of claim 1, wherein said disease or condition is myocardial infarction.

9. The method of claim 1, wherein said disease or condition is stroke.

10. The method of claim 1, wherein said disease or condition is chronic heart failure.

11. The method of claim 1, wherein said disease or condition is diabetic wound healing.

12. The method of claim 1, wherein said composition is administered to a peripheral or central vein.

13. The method of claim 1, wherein said method is combined with intra-arterial administration of SDF-1 or a mutant SDF-1 peptide.

14. The method of claim 1, wherein said disease or condition is tissue damage due to myocardial infarction.

15. The method of claim 1, wherein said composition is administered one or more times until said tissue damage is reduced, repaired, or new blood vessel formation occurs.

16. The method of claim 1, wherein said composition is administered one or more times to ameliorate one or more symptoms of said disease or condition.

17. The method of claim 1, wherein said tissue is a cardiac tissue.

18. The method of claim 1, wherein said tissue is a vascular tissue.

19. The method of claim 1, wherein said SDF-1 comprises the sequence of SEQ ID NO: 69.

20. A method of treating or ameliorating tissue damage in a subject in need thereof, said tissue damage resulting from a disease or condition selected from the group consisting of stroke, myocardial infarction, chronic heart failure, and diabetic wound healing, wherein said method comprises intravenously administering a composition comprising an isolated mutant form of stromal cell derived factor-1 (SDF-1) peptide comprising the formula of a mutant SDF-1 (mSDF-1), mSDF-1-$Y_z$, $X_p$-mSDF-1, or $X_p$-mSDF-1-$Y_z$, wherein said mSDF-1 is a peptide comprising the amino acid sequence of at least amino acids 1-8 of SEQ ID NO:53 and which is optionally extended at the C-terminus by all or any portion of the remaining sequence of SEQ ID NO:53. said SEQ ID NO:53 comprising the amino acid sequence:

(SEQ ID NO: 53)

K P $X_3$ $X_4$ $X_5$ $X_6$ Y R C P C R F F E S H V A R A N V K H

L K I L N T P N C A L Q I V A R L K N N N R Q V C I

D P K L K W I Q E Y L E K A L N K, wherein $X_3$, $X_4$, $X_5$, and $X_6$ are any amino acid, and wherein $X_p$ is a proteinogenic amino acid(s) or a protease protective organic group and p is any integer from 1 to 4;

$Y_z$ is a proteinogenic amino acid(s) or protease protective organic group and z is any integer from 1 to 4;

said mSDF-1 or said mSDF-1-$Y_z$ maintains chemoattractant activity for T cells and is inactivated by matrix metalloproteinase-2 (MMP-2), matrix metalloproteinase-9 (MMP-9), leukocyte elastase, and/or cathepsin G at a rate that is at least 50% less than the rate of inactivation of native SDF-1; and said $X_p$-mSDF-1 or said $X_p$-mSDF-1-$Y_z$ maintains chemoattractant activity for T cells, is inactivated by dipeptidyl peptidase IV (DPPIV) at a rate that is at least 50% less than the rate at which native SDF-1 is inactivated, and is inactivated by MMP-2, MMP-9, leukocyte elastase, and/or cathepsin G at a rate that is at least 50% less than the rate of inactivation of native SDF-1;

wherein said isolated mutant form of SDF-1 peptide does not comprise the amino acid sequence of at least amino acids 1-8 of SEQ ID NO:52 and is administered intravenously in an amount sufficient to treat or ameliorate said tissue damage in said subject.

* * * * *